United States Patent [19]

Kruger

[11] 4,096,142

[45] Jun. 20, 1978

[54] 14,19-DIOXYGENATED STEROID COMPOUNDS AND THEIR 14-DEHYDRO ANALOGS AND PROCESS FOR THE PREPARATION THEREOF

[75] Inventor: Gunther Kruger, St. Laurent, Canada

[73] Assignee: Steele Chemicals Co. Ltd., Pointe Claire, Canada

[21] Appl. No.: 718,921

[22] Filed: Aug. 30, 1976

Related U.S. Application Data

[63] Continuation-in-part of Ser. No. 215,669, Jan. 5, 1972, Pat. No. 3,849,402, and Ser. No. 497,730, Aug. 15, 1974, abandoned.

[30] Foreign Application Priority Data

Jan. 4, 1972  Canada .................................. 131673

[51] Int. Cl.² ............................................. C07J 71/00
[52] U.S. Cl. ...................... 260/239.55 R; 260/397.1; 260/397.3; 260/397.4; 260/397.45; 260/397.47; 260/397.5
[58] Field of Search ..................... 260/239.55 R, 397.1, 260/397.4, 397.45

[56] References Cited

U.S. PATENT DOCUMENTS

| | | | |
|---|---|---|---|
| 3,738,984 | 6/1973 | Lehmann et al. ............... | 260/239.57 |
| 3,752,807 | 8/1973 | Hartenstein et al. ........... | 260/239.57 |
| 3,753,980 | 8/1973 | Haede et al. .................... | 260/239.57 |

*Primary Examiner*—Elbert L. Roberts
*Attorney, Agent, or Firm*—McFadden, Fincham & Co.

[57] ABSTRACT

There are provided novel 14,19-dioxygenated steroid compounds and their 14-dehydro analogs, as well as processes for preparing such compounds. The above compounds are useful as intermediates in the preparation of other steroids, which in turn, may be converted into valuable pharmaceutical agents.

18 Claims, No Drawings

14,19-DIOXYGENATED STEROID COMPOUNDS AND THEIR 14-DEHYDRO ANALOGS AND PROCESS FOR THE PREPARATION THEREOF

This invention relates to chemical compounds and processes for the manufacture of such compounds.

This application is a continuation-in-part of application Ser. No. 215,699, filed Jan. 5, 1972, which issued as U.S. Pat. No. 3,849,402 on Nov. 19, 1974, and application Ser. No. 497,730 filed Aug. 15, 1974.

More particularly, this invention relates to 14,19-dioxygenated steroids and their 14-dehydro analogs.

In the prior art, certain 14$\beta$,19-dioxygenated steroids and their corresponding 14(15)-dehydro and 14$\alpha$-oxygenated analogs are known, which have been obtained by the isolation of certain materials occurring naturally in low concentration in the plant and animal kingdom, which materials are subsequently subjected to chemical transformations, in particular partial degradation. Reference may be had to A. Hunger and T. Reichstein, Helv. 35, 1073 (1952). In such processes, the isolation steps are tedious, afford the desired compounds in only low yields, and are generally difficult due to the chemically labile nature of the latter. Still further, the partial degradation processes of the prior art involves special techniques, such as ozonolysis, and have been performed for only academic interests - i.e. for the structure elucidation of the isolated natural materials.

With the present invention, and according to one aspect thereof, novel compounds unobtainable in the prior art are herewith provided, which novel compounds have the formula

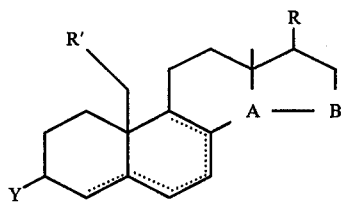

wherein R is selected from the group consisting of O-acyl or O-alkyl; OH; O;

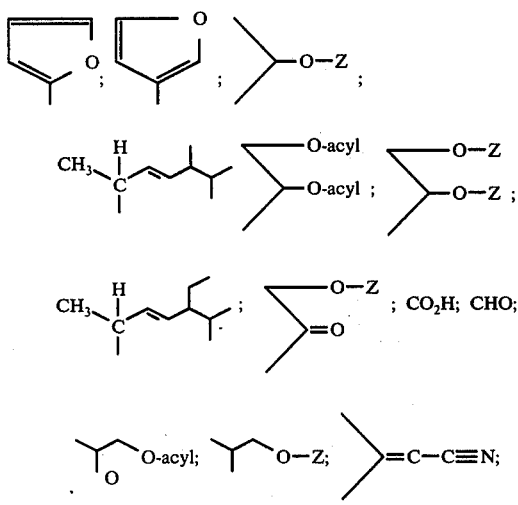

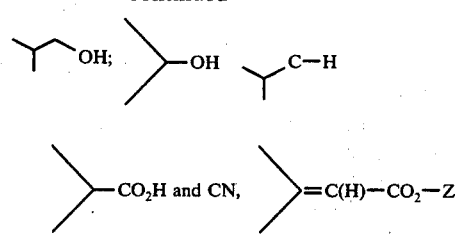

wherein Z is selected from the group consisting of phenyl, halogen, preferably chlorine and bromine, methoxy, $CH_2$=CH and HC≡C; wherein acyl represents a group selected from those consisting of acetate, trimethylacetate, trichloroacetate, trifluoroacetate, or formate, chloroformate, acrylate, methacrylate, 2-furoate, 3-furoate, 2,4-dimethylpyrrole-3-carboxylate, 2,4,5-trimethylpyrrole-3-carboxylate, 2,4-dimethylpyrrole-3-carboxylate 5-carboxylic acid, 2,5-dimethylpyrrole-3-carboxylate, propiolate; Y is selected from the group consisting of 3$\alpha$-hydroxy, 3$\beta$-hydroxy, O=, O-alkyl, O-acyl and H wherein alkyl and acyl are as defined above; the hydrogen atom in the 5-position being 5$\alpha$ or 5$\beta$; R' is selected from the group consisting of hydroxy, CHO, $CO_2H$, CH=NOH,

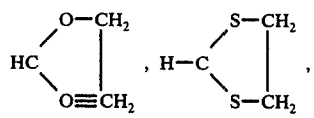

alkyloxy and acyloxy in which the alkyl and acyl groups are as defined above; the groups A and B represent 14- or 15 -carbon atoms, which are either linked by a double bond, or which carry an $\alpha$- or $\beta$-oxido or a 14$\alpha$- or 14$\beta$-hydroxy group, in which case B is a methylene group. The 8-position carries an 8$\alpha$-hydrogen or 8$\beta$-hydrogen atom, and wherein said compound of the formula (I) may include an optional double bond in the 4; 5; 6; 7 and/or 8(9) position.

According to a further embodiment of this invention, there is provided compounds which have the formula

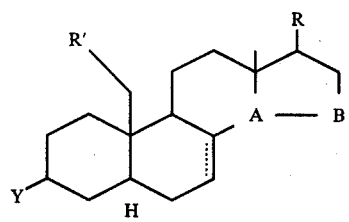

wherein R is selected from the group consisting of O-acyl; OH; O;

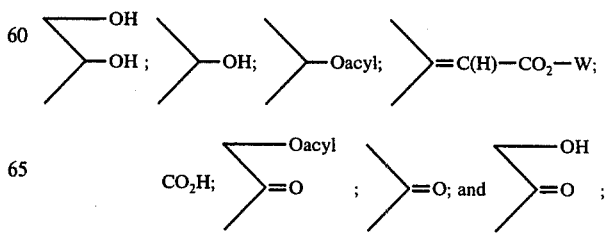

W is methyl or ethyl, wherein acyl represents a group selected from those consisting of formyl, acetyl and lower trialkyl acetyl, wherein the lower alkyl group is methyl or ethyl; R' is selected from the group consisting of hydroxy, oxo and acyloxy wherein acyl is as defined above and the groups A and B represent 14- or 15-carbon atoms, which are either linked by a double bond, or an α- or β-oxido bridge or have a hydroxy group in the 14α- or 14β-position, in which case B is a methylene group or carries a 15α-bromine atom; wherein said dash lines of the Formula represent an optional double bond in the 7(8) position, wherein the wavy line indicates that the hydrogen atom in position 5 is either in α- or β-position; wherein Y is selected from the group consisting of OH, O=, O-tetrahydropyranol ether, O-acyl and H, where acyl is as defined above, and wherein, in the case of R being any of

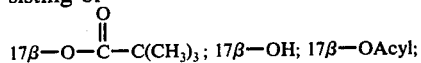

Y is H only.

In the compounds just mentioned, the group R is, in preferred embodiments, selected from the group consisting of 17β—O—C(=O)—C(CH$_3$)$_3$; 17β—OH; 17β—OAcyl;

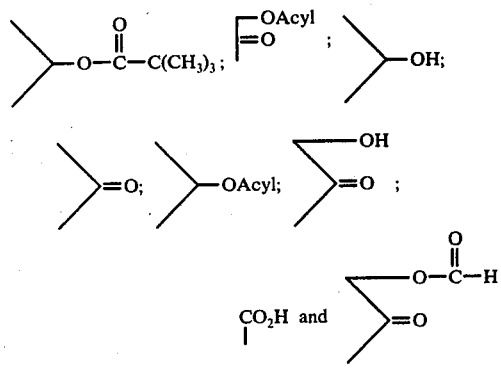

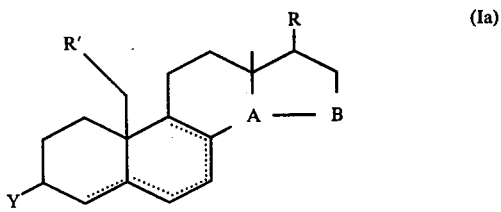

In these preferred compounds where R is as just defined, the radical Y is preferably H in a preferred group of compounds.

According to a further aspect of the present invention, there is provided a process for preparing the above compounds, and in general compounds of the formula

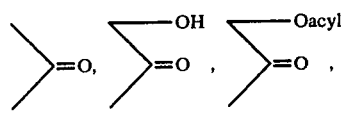 (Ia)

wherein R is selected from the group consisting of O-acyl or O-alkyl; Oh; O;

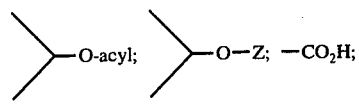

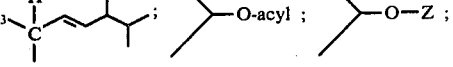

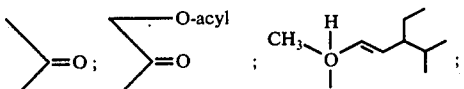

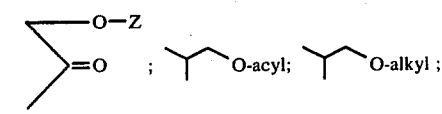

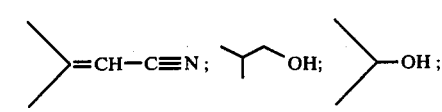

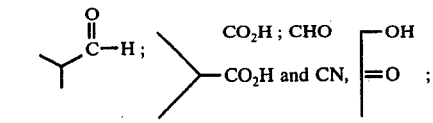

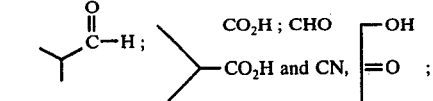

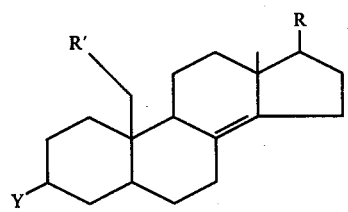

and wherein Z and acyl are as defined above and the other substituents of said compound of the formula (Ia) are as defined hereinabove.

From the above described aspects of the present invention, the present invention commences with naturally occurring inexpensive steroidal raw materials, such as diosgenin, stigmasterol and ergosterol. These compounds are well known for the abundance in which they occur in nature and have for this reason been extensively used for the preparation of economically valuable steroids, e.g. presently nearly all valuable steroid hormones are prepared from these raw materials. Thus, it overcomes the disadvantages of the prior art and, at the same time, provides valuable new compounds as described hereinafter in greater detail.

More particularly, according to the process aspect of the present invention, the process is selected from the group consisting of (a) treating a compound of the formula

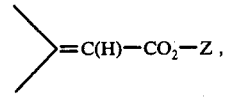 (II)

wherein R, R' and Y are as defined above, with an oxidising agent, to form a compound of the formula (III)

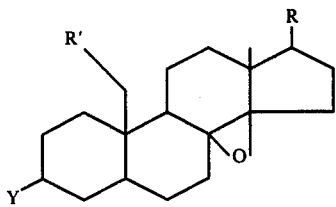

wherein R, R' and Y are as defined above, and subjecting the latter compound to a rearrangement process under hydrogenation or acidic conditions to form a compound of the formula (I) wherein the latter compound contains a 7-double bond and a 14β-hydroxy group;

(b) treating a compound of the formula

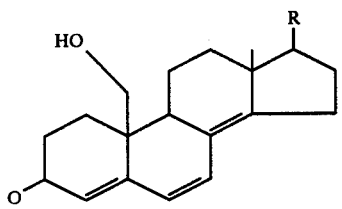

wherein R is as defined above, with an epoxidizing agent to form a compound of the formula

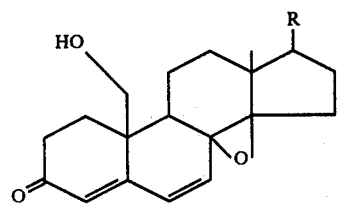

treating the latter with an acetylating agent to form a compound of the formula

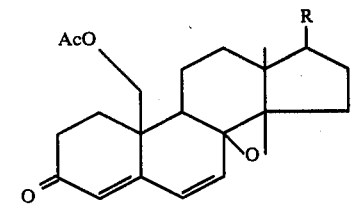

and treating the latter with an acid to form the following compound of formula I

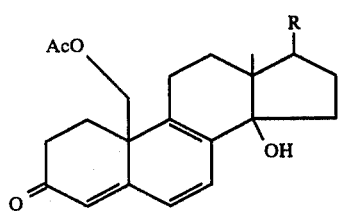

wherein R is as defined above;

(c) reducing a compound of the formula

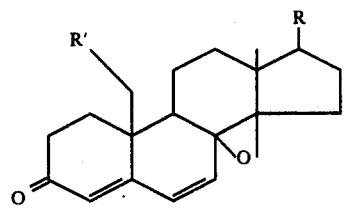

wherein R and R' are as defined above to form a compound of the formula

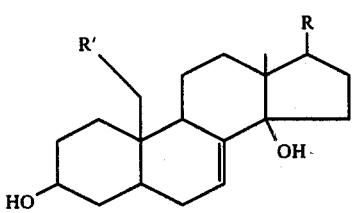

wherein R and R' are as defined above;

(d) reducing a compound of the formula

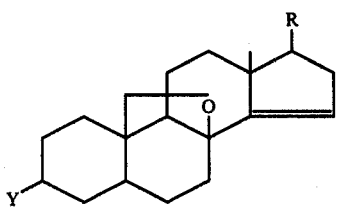

wherein R and Y are as defined above, to form a compound of the formula I,

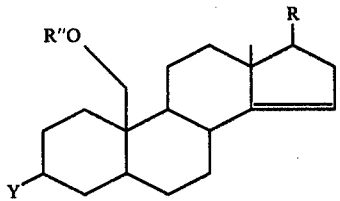

wherein R and Y are as defined above and R" is H or Ac;

(e) subjecting a compound of the formula

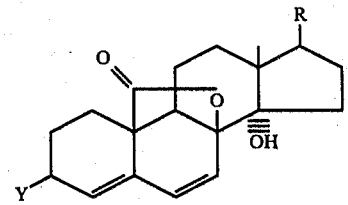

wherein R and Y are as defined above, to hydrogenolysis, to form a compound of the formula

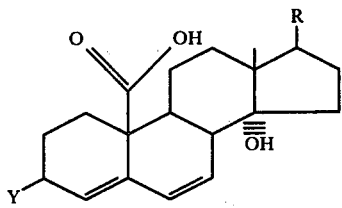

wherein R and Y are as defined above, hydrogenating the latter compound to form a compound of the formula

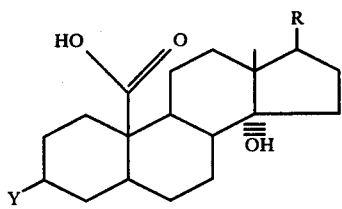

treating the latter with an acid or acid halide to form a compound of the formula

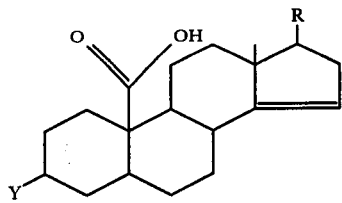

wherein R and Y are as defined above, and treating the latter with a reducing agent to form a compound of the formula I,

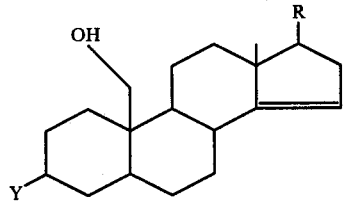

wherein R and Y are as defined above.

In greater detail, and referring to the process aspect of the present invention, process (a) is carried out by treating a compound of the formula II with an oxidizing agent in the initial step. To this end, typical oxidizing agents which may be used are peracids, examples of which are perbenzoic acid, meta-chlorobenzoic acid, peracetic acid, trifluoroacetic acid, perphthalic acid, etc. In general, the oxidizing reaction may be carried out at temperatures ranging from about 100° C to −70° C. The reaction is preferbly carried out in the presence of a non-polar solvent, i.e. one with a small dielectric constant. Typical solvents include hexane, carbon tetrachloride, benzene, etc. Normally, the reaction may be conveniently carried out at room temperature. In the case where the solvents do not completely dissolve the starting material, e.g. when hexane is used as the solvent, elevated temperatures may be employed. It has been found advantageous that the reaction be carried out at relatively high dilution, for example 100 – 2,000 parts of solvent per part of steroid starting material may be employed.

In the second step of this process, wherein the resulting compound of formula (I) is obtained by rearrangement of oxide (III) preferably under hydrogenation conditions, solvents such as acetic acid, propionic acid, methanol or ethanol and catalysts such as palladium or platinum may be employed.

In process (b) the treatment of the compound of formula (IV) with an epoxidizing agent may be carried out under the same or similar conditions as those described above with respect to process (a) to yield the 19-hydroxy-8β,14β-epoxide of formula Va. Thereafter the 19-hydroxy-8β,14β-oxide is acetylated, e.g. using acetic anhydride in pyridine or triethylamine to yield a 19-acetate of the formula (V). The latter compound is then treated with an acid to form the desired end product (I). Any suitable acid may be used which will not, under the reaction conditions, eliminate the 14β-hydroxy group of the end product; for example, strong acids such as para-toluenesulfonic acid, methane sulfonic acid, hydrochloric acid, sulfuric acid, and the like may be employed at high dilution and at low temperatures while conversely, weak acids such as boric acid, acetic acid, propionic acid, or formic acid may be employed at higher concentrations at elevated temperatures.

In carrying out the process (c), a compound of the formula (VI), prepared as described above, is initially reduced with a metal hydride to form a corresponding 3β-hydroxy-8β,14β-oxido-4,6-diene. This step may be carried out using sodium borohydride with a suitable alcohol such as methanol, or alternately, lithium tri-t-butoxyaluminum hydride in tertiary butanol or tetrahydrofuran, etc. Preferably, temperatures between −10° C. and room temperature are employed. Subsequent reduction, e.g. by treatment with molecular hydrogen and a noble metal catalyst thereafter yields a compound of the formula (I) possessing a 7 double bond and a 14β-hydroxy group.

By terminating the reduction at an early stage, a compound of the formula (III) described above, can be obtained which may subsequently be treated as described in process (a) to yield a desired end product of formula (I), having a 7 double bond.

In a preferred embodiment of process (c) the intermediate 3-hydroxy-4,6-diene obtained by reduction with a metal hydride, is not isolated but further reduced to a compound of formula (I) by addition of a noble metal catalyst, e.g. palladium on charcoal, and subsequent agitation in an atmosphere of hydrogen.

In process (d) reduction of a compound of formula (VII) may be carried out with finely divided zinc in the presence of an aqueous carboxylic acid, e.g. aqueous acetic acid, propionic acid, formic acid or the like to form the desired end product. Employing the above aqueous carboxylic acids there has been found that the reaction will yield predominantly the 19-hydroxy-14-enes of formula (I). If water-free acids, as well as mixtures of these with the corresponding anhydrides, are employed, it has been found that the corresponding 19-acylates of formula (I) can be major products. The temperatures employed in the reaction are preferably elevated - e.g. they may range from about 50°-100°C.

With respect to process (e), the hydrogenolysis of the compounds of the formula (VIII) to 19-carboxylic acids of formula (X) via carboxylic acids of formula (IX) will be carried out by conventional techniques, e.g. by catalytic hydrogenation or with a dissolving metal such as zinc or an alkali metal. In the case compounds of formula (VIII) are subjected to hydrogenation conditions hydrogenolysis is accompanied by saturation of the olefinic double bonds to yield directly compounds of formula (X). In the case dissolving metals are employed it may be necessary to subject the hydrogenolysis product containing compounds of formula (IX), to hydrogenation conditions to yield (X). In the subsequent step, the latter compound is treated with an acid or an acid halide as, for example, thionyl chloride, dry hydrogen chloride, benzoyl chloride, phosphorous oxychloride, etc. whereby the 14α-hydroxy group is eliminated and a 14(15) double bond introduced to yield compounds of formula (XI). In the case where Y is O, the latter compounds can be further reduced with a metal hydride, e.g. lithium aluminum hydride to yield the corresponding alcohols having Y = OH.

The various products obtained from the abovedescribed processes (a) to (e) may be converted, if desired, into other novel products of the present invention. Thus, for example, where the products obtained of formula I have a 3-keto group, this group may be reduced to form the corresponding 3-hydroxy compound using, for example, sodium borohydride in the presence of an inert solvent such as methanol. For greater detail of such reduction reactions, reference may be had to Fieser & Fieser Reagents for Organic Synthesis, 1967, page 1049. Likewise, where the end product of formula I is unsaturated in the 4, 5 and 6 position, the product may be hydrogenated using, for example, palladium on charcoal in a hydrogen atmosphere - for greater detail, reference may be had to Fieser & Fieser (supra) page 778. In this respect, it has been found that when the 3-keto group reduction process is carried out before the 4,6-diene hydrogenation process, more of the corresponding 5α-hydrogen steroids of formula I will be obtained, while when the reduction of the 3-keto group is carried out subsequently to the hydrogenation of the double bonds in the 4,6 position, conversely, more of the corresponding 5β-hydrogen steroids of the formula I will be obtained.

In addition, the compounds of formula I having a 14α-hydroxy group, may be converted to compounds of formula I having a double bond in the 14-position. To this end, the 14α-hydroxy compounds of formula I may be treated with thionyl chloride in pyridine, as for example described in Fieser & Fieser (supra) page 1084. In turn, when the substituents A and B represent carbon atoms 14 and 15 linked by a double bond, such compounds of formula I may be converted to the corresponding 14α-hydroxy compounds according to, for example, Fieser & Fieser, page 1083. To this end, briefly summarized, such 14-dehydrosteroids may be initially converted to the corresponding 14β-ol, 15β-bromo adducts by treatment with hypobromous acid following which the latter adduct is converted to the corresponding 14β,15β-epoxide by treatment with a base. The epoxide may then be hydrogenolysed by treatment with a metal hydride (such as aluminum hydride - see page 599 of Fieser & Fieser supra) or by catalytic hydrogenation.

The 4,6,8(14)-triene-3-ones of Formula IV used as the starting materials for process (b) may be obtained from the corresponding known (K. Heusler et al, Experiencia, 18, 460 (1962)) 19-hydroxy-4,6-diene-3-ones by treatment with a strong base in dimethyl sulfoxide and subsequent treatment of the resulting enolate anion with a dehydrogenating agent, e.g. chloranil or 2,3-dichloro-5,6-dicyanoquinone. The 8(14)-enes of Formula II used as starting materials for process (a) may be obtained from the above 4,6,8(14)-triene-3-ones by successive reduction with sodium borohydride and catalytic hydrogenation. The 8,19-oxido-14-enes of Formula VII used as starting materials for process (d) may be obtained from 19-hydroxy steroids as described by D. Hauser et al in Helv. 47, 1961 (1964). For process (e), the starting materials may be obtained from the teachings of copending application Ser. No. 497,729, filed August 15, 1974.

The novel products of the present invention of formula (I) are valuable as intermediates for the preparation of compounds of the formula

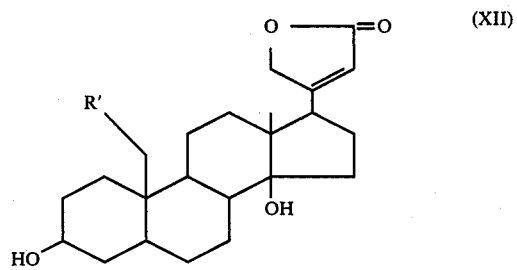

wherein R' is as defined above.

The use of such compounds and their glycosides for the treatment of cardiac insufficiency is well known, as for example disclosed in Angewandte Chemie vol. 9, No. 5, pp 321–332. Conventionally, such 14β-hydroxycardenolides have been isolated from natural sources. Recently a number of 14β-hydroxycardenolides have also been obtained by synthesis using as key intermediates 14β-hydroxypregnan-20-ones or pregn-14-en-20-ones. These synthetic methods are, however, not very economical and afford only cardenolides having a methyl group in position 10. In contrast, the present invention provides valuable 14-functionalized 19-oxygenated precursors to 19-oxygenated 14β-hydroxy cardenolides by novel and economical routes in which the 19-oxygen atom assists in chemical transformations instead of encumbering them.

As is obvious to those skilled in the art, these precursors can readily be converted into the corresponding 14β-hydroxycardenolides by taking recourse to one or several of the well known previously developed methods for such conversions. These methods together with the methods of this patent application allow the preparation of variously functionalized cardenolides, such as, for example, 19-oxygenated cardenolides, 19-noncardenolides and unsaturated cardenolides and thus make it possible to bring about a medicinally desirable change in the kind and degree of cardiac activity. For example, studies on differently substituted cardenolides isolated from natural sources have shown that 19-oxygenated cardenolides are substantially more active then their 19-methyl-analogs, as described in Fieser and Fieser, Steroids, Chapter 20.

The conversion of the group R in position 17 of the 14-functionalized 19-oxygenated precursors of this invention into the 17β-butenolide ring of the compounds of formula (XIII) may be carried out according to methods known to those skilled in the art, as for example summarized in Angewandte Chemie Vol. 9, No. 5, pp 321–332. Thus, for instance, 14β-hydroxy-17β-acetyl- as well as 14β-hydroxy-21-acetoxy-17β-acetyl steroids have been converted into 14β-hydroxy compounds having a butenolide ring in the 17β-position via initial transformation into the corresponding 20-ethoxyacetylen-20-ol and subsequent acid treatment which is, in the case of the 17β-acetyl steroids, followed by oxidation with selenium dioxide in boiling benzene, as described by F. Sondheimer, Chemistry in Britain, Vol. 1, No. 10, pp 454–464 (1965). While in the above method the butenolide side chain is introduced subsequent to the introduction of the 14β-hydroxy group, in other methods, as for example, described in Angewandte Chemie (supra), the 17β-butenolide side chain is introduced into compounds, such as the 14 -dehydro analogs, not possessing a 14β-hydroxy group which is introduced in subsequent steps.

With regard to the other groups in the 17β-position, as specified above for general formula (I), where the group R is $CH_2Oacyl$ —CO it may be converted into the butenolide ring by the method described above for the transformation of a 21-acetoxy-17β-acetyl steroid (R is $CH_2OAc$ —CO). Where the group R is $CH_2Oalkyl$ —CO it may be first converted to a group R where it is $CH_2OH$ —CO by conventional methods. Subsequent acetylation affords then the above 21-acetate (R is $CH_2OAc$ —CO) which then can be converted to the butenolide ring as described above. In the case where R is $CH_2Oacyl$ —CH —acyl or $CH_2Oalkyl$ —CH—Oalkyl conversion of these groups by conventional methods into group R where it is $CH_2OH$ —CHOHC followed by selective acetylation in position 21 and subsequent oxidation of the 20-hydroxy group by the method described, for example, in F. Sondheimer, Chemistry in Britain, cited above, affords then a group R which is $CH_2OAC$ —CO, which may be converted to a butenolide ring according to the methods described above.

In the case where R is $CH_3$—CH—Oacyl, $CH_3$—CH—Oalkyl or $CH_3$—CH—OH conventional procedures, such as used for the generation of hydroxy groups from acylates and ethers respectively and subsequent oxidation, afford a 17β-acetyl group (where R is $CH_3$—CO), which may be converted to the butenolide ring by methods described above.

In the case where R is $CH_3$—CH—CHO the 17β-butenolide ring may be formed by conventional cyanohydrin formation followed by dehydration and conversion of the α,β-unsaturated nitrile obtained into the corresponding α,β-unsaturated 23-carboxylic acid ethyl ester, again by conventional methods, and subsequent treatment with selenium dioxide in boiling benzene as described by F. Sondheimer, Chemistry in Britain, cited above. In the case where R is $CH_3$—CH—$CH_2$Oacyl or $CH_3$—CH—$CH_2$Oalkyl conversion to the corresponding 22-alcohol, where R is $CH_3$—CH—$CH_2$OH and oxidation to the above aldehyde, R being $CH_3$—CH—CHO, by conventional methods, may then afford the 17β-butenolide ring by the method described above. In the case where R is $CH_3$—CH—$CO_2H$, reduction of the carboxylic acid group to the above 22-aldehyde by conventional methods may then subsequently afford the 17β-butenolide ring by the method described above.

In the case where R is $CH_3$—CH—CH=•CH—CH($CH_3$)—CH($CH_3$)$_2$ or $CH_3$—CH—CH=•CH—CH($CH_2CH_3$)—CH($CH_3$)$_2$ ozonolysis of the 20(22)-double bonds, as described, for example, by A. F. Daglish J. Chem. Soc., pp 2627–2633 (1954) affords then the above 22-aldehyde, R being $CH_3$—CH—CHO, which may then be converted to the butenolide ring by the method described above.

In the case where R is CN, conventional transformation to the corresponding methyl ester, R being $COOCH_3$, followed by conversion of the latter to a butenolide ring may be accomplished as described by F. Sondheimer, Chemistry in Britain, cited above. In the case where R is O= formation of the corresponding cyanohydrin followed by conventional dehydration and hydrogenation, affords R being CN which can be converted to the 17β-butenolide ring as described above. In the case where R is OH, -Oacyl or -Oalkyl conversion of these groups into compounds where R is O= by conventional methods followed by application of the methods described above also yields the 17β-butenolide ring.

The various processes of the present invention possess several unexpected and advantageous features. Thus it is a special advantageous feature of process (a) that the 19-hydroxy-8(14)-enes as well as the 19-acetoxy-8(14)-enes of structure (II) yield, under the preferred conditions, predominantly the corresponding 8β,14β-oxides of structure (III). This is in contrast to previous experiences (L. F. Fieser, M. Fieser, Steroids, Reinhold Publishing Corp., New York, 1967, pp. 239–241). The formation of 19-hydroxy-8β,14β-oxides can be rationalized by assuming that the 19-hydroxy group exerts a cis-directing effect on the epoxidation by association with the epoxidizing agent, (H. B. Henbest, R. A. L. Wilson, J. Chem. Soc. (1957) 1958) and that this effect is stronger than the trans-directing effect of the 10β- and 13β-methyl groups by steric repulsion of the reagent from the 8β-position. The trans-directing effect of 10β- and 13β-methyl groups on the approach of reagents towards carbon atoms situated one but next to the 10- or 13- position, e.g. towards the 8-carbon atom, has been well established (see for example the reference above and also G. H. Alt and D. H. R. Barton, J. Chem. Soc. (1954) 1356); also evidence has been obtained for the cis-directing effect of 19-hydroxy groups on the epoxidation of 5-enes (M. Mousseron-Canet, M. M. B. Lobeeuw, J. C. Lanet, C. R. Acad. Sc. Paris, t 262, Serie C, p 1438 (1966)) and 7-enes (Patent Application 1505-8)) though in the epoxidation of 19-hydroxy-7-enes this effect appears to be too weak to overcome effectively the two-fold steric repulsion of the 10β- and 13β-methyl group. By contrast no cis-directing effect of 19-acetoxy groups has yet been observed and experimental evidence suggests that, if it is present, it is much weaker than that of the 19-hydroxy group (vide infra, process (b); M. Mousseron-Canet, B. Lobeeuw, Bull. Soc. France, 2746 (1964, No. 11)).

It is thus even more surprising that in the epoxidation, albeit under the preferred reaction conditions, of 19-acetoxy-8,14-enes predominantly 8β,14β-epoxides can be formed. Possibly weak association of the epoxidation reagent with the 19-acetoxy group in conjunction with the trend of unsaturated ring junctions between 6- and 5-membered rings to form a cis-junction on saturation, e.g. by epoxidation (J. Joska, J. Fajkos, F. Sorm, Collection Czech. Chem. Commun., 31, No. 1, 298 (1966)) or hydrogenation, leads to the unexpected 8β,14β-oxide formation.

It is another special advantage of the method of process (a) that practically no rearrangement of the 8β,14β-oxides has been observed as in the case of the 8α,14α-epoxides (L. F. Fieser, M. Fieser, Steroids, p. 243). It is still another advantage of process (a) that it allows the selective conversion of initially formed isomeric 8α,14α-epoxides, which are very similar in their properties to the 8β,14β-oxides, into the corresponding 8,19-oxido-14α-alcohols which have rather different properties. Owing to the enhanced difference in the properties of the major product and its chief by-product, the purification of the former is then greatly facilitated.

It is an unexpected finding that treatment of the 8β,14β-oxides under hydrogenation conditions leads to rearrangement and the formation of the corresponding 14β-hydroxy-7-ene rather than to hydrogenolysis of the epoxide. Such rearrangement would generally be expected to take place by acid treatment, which, however, would be expected to promote subsequent dehydration of the initially formed 14β-hydroxy-7-ene, since the latter is a tertiary allylic alcohol. It is a special advantage of the method or preparing the 14β-hydroxy-7-enes from the corresponding 8β,14β-oxides, that it proceeds in high yield and takes place without concomitant dehydration of the desired 14β-alcohol. If desired, the 14β-hydroxy-7-enes can further be subjected to hydrogenation condition to yield the corresponding saturated 14β-alcohol.

With regard to process (b) it is a special advantage that, employing the preferred conditions, the epoxidation of the 19-hydroxy-4,6,8(14)-triene-3-ones yields predominantly the corresponding 8β,14β-oxido-4,6-dien-3-ones.

In contrast to the 8(14)-enes of process (a) the 4,6,8(14)-trienes of process (b) yield predominantly, i.e. generally almost conclusively, the corresponding 8α,-14α-oxides when the hydroxy group is converted to a 19-acetoxy group of a 19-aldehyde, which is in agreement with the trans-directing effect of bulky groups in the 10β- and 13β-position (vide supra). It is surprising that the latter effect can be overcome by the cis-directing effect (vide supra) of the 19-hydroxy group.

It is one of the advantages of the epoxidation of the 4,6,8(14)-en-3-ones by the method of process (b) that the 8β,14β-oxido-4,6-dien-3-ones are often not contaminated by the corresponding 8α,14α-oxides, which are very similar in their properties and would thus be expected to make the purification of the 8β,14β-oxides difficult. Instead of the 8α,14α-oxides the isomeric 14α-hydroxy-8,19-oxides are then found as by-products, which are chemically rather different from the 19-hydroxy-8β,14β-oxides and hence can readily be separated. In the case the 19-hydroxy-8α,14α-oxides are present they can be selectively converted to the corresponding 14α-hydroxy-8,19-oxides by mild acid treatment which leaves the 19-hydroxy-8β,14β-oxides unaffected.

Thus treatment of the above reaction mixture with acetic anhydride and pyridine leads to the selective conversion of the 19-alcohols to the corresponding 19-acetates, while the tertiary 14α-alcohols, present as by-products, remain unaffected and can be readily separated by precipitation with petroleum either from an ethereal solution of the unpurified product.

It is a still further advantage of the preferred epoxidation conditions of process (b) that they allow the selective epoxidation of the 8(14)-double and leave practically the 4- and 6-double bonds uneffected. While it has previously been shown, that under carefully controlled conditions 4,6-dienones can be epoxidized selectively to the corresponding 6,7-oxido-4-en-3-ones, it cannot be predicted that the analogous epoxidation of the 8(14)-double bond in the 4,6,8(14)-trien-3-ones would proceed in the same selective manner, especially if one considers that the electron withdrawing effect of the 3-keto group, which can be made responsible for the selective epoxidation of the 4,6-dien-3-ones by denuding the 4-double bond more of electrons than the 6-double bond, would be expected to produce a considerably decreased differentian between the electron densities at the 6- and 8(14)-double bonds, since it is situated further away from these double bonds than from the 4,6-double bond system.

It is yet another advantage of the preferred epoxidation method of process (b) that under the reaction conditions no rearrangement takes place as observed previously in the epoxidation of 8(14)-enes (L. F. Fieser, M. Fieser, Steroids p. 243). This absence of decomposition by rearrangement is the more noteworthy, since the epoxides of process (b) possess an allylic double bond in position 6, which should greatly facilitate such rearrangements.

It is especially surprising that by carrying out the epoxidations, as done in the preferred method, in solvents, such as hexane or carbon tetrachloride rather than in the more polar solvents, such as methylene chloride, chloroform or ether, or mixtures of these with methanol, which are commonly employed in epoxidations, and that by carrying out the epoxidations at a greater dilution than usual, considerable improvements in the yields of the desired 8β,14β-epoxides are obtained. These improvements in yield allow the synthesis of 8β,14β-oxides on a preparative scale and without taking recourse to laborious and costly isolation procedures, such as chromatography.

The improvement in yields 8β,14β-oxides by changing from a more polar to a less polar solvent may be rationalized by assuming that the association between the 19-hydroxy group and the epoxidizing agent is considerably enhanced in the less polar solvents as their molecules exhibit a reduced tendency for competitive association with the epoxidizing agent. The improvement in yields by carrying out the epoxidation at an increased dilution could possibly be due, in part, to the fact that the acid catalysed rearrangements of the 8β,14β-oxides formed is more dependent on the concentration of the reagent than the epoxidaton of the 8(14)-double bond so that less by-products are formed.

It is surprising that in the acid treatment of 8β,14β-oxido4,6-dien-3-ones of formula V the corresponding 14β-hydroxy-4,6,8(9)-trien-3-ones can be obtained without concomitant dehydration of the latter under the reaction conditions. This may be rationalized by assuming that, in contrast to the saturated 8,14-epoxide of formula (III), the 8β,14β-oxide bridge in the starting dienes is activated by the presence of the allylic double bond in position 6(7) so that only relatively weak acidic conditions are required for its rearrangement i.e. conditions under which the rearrangement product does not suffer dehydration.

It is an unexpected finding of process (c) that the hydrogenation of the intermediate 3β-hydroxy-8β,14β-oxido-4,6-dienes affords largely the corresponding 3β,14β-dihydroxy-7-enes of formula (I) of te 5α-hydrogen series since previous studies on the hydrogenation of 3β-hydroxy-4-enes have shown that the latter tend to yield preferentially 4,5-dihydro products of the 5β-hydrogen series (C. W. Shoppee, B. C. Agashe and G. H. R. Summers, J. Chem. Soc., (1957) 3107). It is a special advantage of the above reduction and hydrogenation reactions that they can be carried out in one vessel, i.e. that after completion of the reduction the hydrogenation catalyst is added to the mixture, which is then agitated in an atmosphere of hydrogen. The conversion of the 8β,14β-oxido-4,6-dien-3-ones of formula (VI) to the corresponding 3β,14β-hydroxyl-7-enes of formula (I) can thus, for practical purposes, be considered as a one-step reaction rather than a two-step reaction and thus becomes considerably more economical.

With regard to process (d) it is surprising that 8,19-oxido-14-enes can be hydrogenolysed with zinc in acetic acid, since generally the hydrogenolysis of a carbonoxygen bond by zinc requires the activation by a carbonyl group (see for example L. F. Fieser and G. Fieser, Reagents for Organic Synthesis, John Wiley and Sons, Inc., 1967, pp. 1277 and 1278). It is further surprising that under the reaction conditions the originally liberated 19-hydroxy group is acetylated. Apparently the acetylation by acetic is promoted by zinc, since, according to general practice, heating of steroid alcohols below 100° in acetic acid only very slowly leads to the formation of the corresponding acetates.

It is a further special advantage of process (d) that the acetylation of the 19-hydroxy group during the hydrogenolysis with zinc can, if so desired, be suppressed by the addition of water. The formation of the 19-hydroxy group by hydrogenolysis is of considerable synthetic value because it leaves other acyloxy groups in the molecule uneffected. Thus in the hydrogenolysis of 3-acetoxy-8,19-oxido-14-enes, 3-acetoxy-19-hydroxy-14-enes are formed, which cannot be formed by selective hydrolysis of the corresponding 3,19-diacetates. The 19-hydroxy group can thus be modified without effecting the 3-position, e.g. it may be converted to 19-aldehydes such as present in potent cardiac-active cardenolides (vide supra).

It is also unexpected that the addition of water, in addition to preventing acetylation, greatly enhances the reaction rate and thus facilitates the method of process (d). Still further, the inclusion of aqueous copper salts enhances even further the reaction rate.

It is a special advantage of process (e) that the hydrogenolysis of the 19,8-lactone of formula (VIII) is activated by the carbonyl group in position 19. It is a further advantage of process (e) that the intermediate 3-oxo-4,6-dien-19-oic acid can be employed for the preparation of the corresponding 19-nor analogs. As is well known, 19-nor steroids show often superior physiological activity over the corresponding analogs possessing 19-carbon atoms and are also more readily amenable to total synthesis from simple cheap non-steroidal starting materials (see for example, L. F. Fieser and M. Fieser, Steroids, p. 697, and R. Wiechert, Angew. Chemie, Int. Edn., 9, 321 (1970) respectively).

Having thus generally described the invention, reference will now be made to the accompanying examples which illustrate preferred embodiments of the invention.

EXAMPLE 1

A mixture of 2.7 g of 3β,19-dihydroxy-17β-pivaloxy-5α-androst-8(14)-ene, 2.1 g of meta-chloroperbenzoic acid and 2.7 l of carbon tetrachloride was left to stand at room temperature for 4.5 hours, whereupon it was 3 times extracted with 100 ml of 2% aqueous potassium hydroxide and once with 120 ml of water. Drying over sodium sulfate followed by evaporation, treatment of the gelatinous residue obtained with hexane and filtration gave 2.57 g of a material, mp 135°–139°, consisting essentially of 3β,19-dihydroxy-8β,14β-oxido-17β-pivaloxy-5α-androstane and containing 3β,14α-dihydroxy-8,19-oxido-17β-pivaloxy-5β-androstane as a by-product. This material was employed for the reaction of Example 2. Recrystallisation from ether-hexane gave the purified product, mp 148°–153° C.

EXAMPLE 2

A mixture of 2.0 g of the product obtained as described in Example 1, 6.0 ml of pyridine and 3.0 ml of acetic anhydride was stirred under nitrogen at room temperature for 16 hours whereupon 18 ml of water was added. Extraction with ether, followed by repeated extraction of ethereal phase with water and evaporation at reduced pressure gave a residue which crystallised on treatment with ether and hexane. Filtration and subsequent recrystallisation from methanol gave 1.29 g of 3β,19-diacetoxy-8β,14β-oxido-17β-pivaloxy-5α-androstane, mp 167°–169° C which was used for the reaction described in Example 8. Thick-layer chromatography of the mother liquors on silica gel gave, on elution with ethyl acetate-benzene 1:4, a fraction, which on recrystallisation with ether-hexane afforded additional material of the above compound, mp 173°–174°. Subsequent elution with the same solvent system gave, after recrystallisation from ether-hexane, 3β-acetoxy-14α-hydroxy-8,19-oxido-17β-pivaloxy-5α-androstane, mp 208°–209° C, as well as a compound of unknown structure, presumably 14α-hydroxy-8,19-oxido-17β-pivaloxy-5α-androstane or 14α-hydroxy-8,19-oxido-17β-pivaloxy-5α-androstan-3-one, mp 150°–154° C.

EXAMPLE 3

A mixture of 1 g of 3β,19-diacetoxy-8β,14β-oxido-17β-pivaloxy-5α-androstane, 50 ml of acetic acid and 500 mg of 5% palladium on charcoal was shaken in an atmosphere of hydrogen for 24 hours, whereupon 300 ml of ether was added and the mixture was filtered through celite. The filtrate was cooled in an ice-bath and 160 ml of potassium hydroxide-water 1:1 was added. After some stirring the ether phase was washed twice with 100 ml of water. The ether phase was then treated with cellulose powder, filtered through celite and evaporated at reduced pressure. Treatment with ether and hexane gave 391 mg of a precipitate, mp 152°–153°, which, after recrystallisation from ether hexane, gave the purified sample of 3β,19-diacetoxy-14β-hydroxy-17β-pivaloxy-5α-androstane, mp 155°–156° C, as verified by spectroscopic and elemental analysis as well as by mass-spectroscopy. Thick layer chromatography of the mother liquors on silica gel gave on elution with ethyl acetate-benzene 1:10 3β,19-diacetoxy-17β-pivaloxy-5α-androst-8(14)-ene, 115°–117° C as well as a subsequent fraction consisting of a compound considered to be 3β,19-diacetoxy-17β-pivaloxy-5α-androstane or its 8α-hydrogen isomer.

EXAMPLE 4

A mixture of 190 mg of 3β,19-diacetoxy-8β,14β-oxido-17β-pivaloxy-5α-androstane, 38 mg of 5% palladium on charcoal and 6 ml of acetic acid was shaken in an atmosphere of hydrogen for 4 hours; the mixture was then filtered through diatomaceous earth. The filter cake was washed with 3 ml of acetic acid and 3 ml of water was added to the combined solutions. The mixture was left to stand at −5° C and was then filtered yeilding 176 mg of a white precipitate. Recrystallisation of the latter from ether-petroleum ether gave 121 mg of 3β,19-diacetoxy-14β-hydroxy-17β-pivaloxy-5α- androst-7-ene, mp 141°–142° C, as evidenced by ir and nmr-spectroscopy.

EXAMPLE 5

A mixture of 2 mg of 3β,19-diacetoxy-14β-hydroxy-17β-pivaloxy-5α-androst-7-ene, 1 mg of 5% palladium on charcoal and 0.2 ml of acetic acid was shaken in an atmosphere of hydrogen for 16 hours whereupon it was diluted with water, made basic with aqueous potassium hydroxide and extracted with ether. Evaporation of the ethereal phase gave 3β19-diacetoxy-14β-hydroxy-17β-pivaloxy-5α-androstane and, as a by-product, 3β,19-diacetoxy-17β-pivaloxy-5α-androst-8(14)-ene as evidenced by tlc.

EXAMPLE 6

This experiment was carried out as Example 5 except that instead of the palladium on charcoal, platinum oxide was used as the catalyst. Tlc analysis showed that, in addition to the products formed in Example 5, a further compound was formed, considered to be the 8-isomer of the 14β-alcohol of Example 5.

EXAMPLE 7

A mixture of 20 mg of 3β,19-dihydroxy-8β,14β-oxido-17β-pivaloxy-5α-androstane, 1 ml of benzene and 1 ml of a 70% solution of sodium bis (2-methoxyethoxy) aluminium hydride in benzene was left to stand at room temperature for 1 hour whereupon the excess of reducing agent was destroyed by gradual addition of small amounts of water. The mixture was then treated with ethyl acetate and methanol and filtered. The filtrate was evaporated and the residue obtained which contained 8β,14β-oxido-3β,17β,19-trihydroxy-5α-androstane as the steroidal material, was dried at a vacuum for 16 hours and was then left to stand with 0.04 ml of acetic anhydride and 0.08 ml of pyridine under nitrogen for 16 hours. The mixture was then treated with 10 volumes of water and extracted with ether. The ether solution was extracted several times with water and evaporated at reduced pressure. Recrystallisation of the residue obtained with hexane gave 3β,17β,19-triacetoxy-8β,14β-oxido-5α-androstane, mp 134°–136° C.

EXAMPLE 8

A mixture of 10 mg of 3β,19-dihydroxy-8βroom β-oxido-17β-pivaloxy-5α-androstane and 0.1 ml of 2 normal methanolic potassium hydroxide was heated at 69° C. for 20 hours whereupon 0.1 ml of 2 normal acetic acid in ethyl acetate was added. The mixture was evaporated at reduced pressure and dried at high vacuum. The residue obtained, which besides potassium acetate, contained 8β,14β-oxido-3β,17β,19-trihydroxy-5α-androstane, was left to stand at 3βtemperature with 0.2 ml of pyridine and 0.1 ml of acetic anhydride under nitrogen for 16 hours. The mixture was then treated with water and extracted with ether. The ethereal phase was extracted several times with water and evaporated at reduced pressure. The residue obtained crystallized on treatment with aqueous methanol yielding 3β,17β,19-triacetoxy-8β,14β-oxido-5α-androstane as evidenced by comparison of its ir spectrum with that of the product obtained in Example 7.

EXAMPLE 9

A mixture of 25 mg of 3β,17β,19-triacetoxy-5α-androst-8(14)-ene, 12.5 ml of carbon tetrachloride and 25 mg of metachloroperbenzoic acid was left to stand at room temperature for 16 hours whereupon it was several times extracted with dilute aqueous potassium hydroxide. Evaporation of the organic phase gave a residue which crystallized on treatment with hexane yielding 3β,17β,19-triacetoxy-8β,14β-oxido-5α-androstane as evidenced by comparison of its ir spectrum with that of the product obtained in Example 7. Tlc analysis of the mother liquor of the product obtained revealed the formation of another closely related compound which was considered to be the isomeric 3β,17β,19-triacetoxy-8,14-oxido-5α,8α,14α-androstane.

EXAMPLE 10

A mixture of 70 mg of 3β19-diacetoxy-17β-pivaloxy-5α-androst-8(14)-ene, 70 ml of carbon tetrachloride and 52.5 mg of meta-chloroperbenzoic acid was left to stand at room temperature for 16 hours and then for three days at 5° C whereupon it was extracted three times with 50 ml of 2% aqueous potassium hydroxide. Evaporation at reduced pressure followed by recrystallization from hexane-ether gave 3β,19-diacetoxy-8β,14β-oxido-17β-pivaloxy-5α-androstane as evidenced by comparison of its ir spectrum with that of the product obtained in Example 2.

EXAMPLE 11

A mixture of 20 mg of 3β,19-diacetoxy-14β-hydroxy-17β-pivaloxy-5α-androst-7-ene and 1.0 ml of 0.2 N methanolic potassium hydroxide was heated under nitrogen at 70° C. for 20 hours whereupon a solution of 0.2 N acetic acid in ethyl acetate was added and the mixture was evaporated. The residue obtained was treated with water and the mixture was then extracted with ethyl acetate. Evaporation of the ethyl acetate solution gave 3β,14β,17β,19-tetrahydroxy-5α-androst-7-ene as indicated by tlc analysis.

EXAMPLE 12

A mixture of 20 mg of the product obtained in Example 11, 0.1 ml of acetic anhydride, and 0.2 ml of pyridine was left to stand at room temperature under nitrogen for 16 hours whereupon water was added and the mixture was extracted with ether. The ethereal phase was extracted several times with water and then evaporated yielding 3β,17β,19-triacetoxy-14β-hydroxy-5α-androst-7-ene as indicated by tlc analysis.

EXAMPLE 13

A mixture of 50 mg of 3β17β,19-triacetoxy-8β,14β-oxido-5α-androstane, 10 mg of 5% palladium on charcoal and 1.5 ml of acetic acid was shaken in an atmosphere of hydrogen for 23 hours whereupon the mixture was diluted with ether and filtered through celite. Evaporation of the filtrate gave a product containing, besides starting material, 3β,17β,19-triacetoxy-14β-hydroxy-5α-androst-7-ene as indicated by tlc comparison with the product obtained in Example 11 by a different route.

EXAMPLE 14

A mixture of 30 mg of 3β,19-diacetoxy-14β-hydroxy-17β-pivaloxy-5α-androstane and 3.0 ml of 0.2 N methanolic potassium hydroxide was heated at 70° C. for 16 hours under nitrogen whereupon the mixture was neutralized with 0.2 N glacial acetic acid in ethyl acetate and evaporated to dryness at reduced pressure. The residue obtained was treated with ethyl acetate and filtered through diatomaceous earth. Evaporation of the filtrate yielded 3β,14β,17β,19-tetrahydroxy-5α-androstane as indicated by tlc analysis.

EXAMPLE 15

Acetylation of the product obtained in Example 14 by the method described in Example 12 afforded 3β,17β,19-triacetoxy-14β-hydroxy-5α-androstane as indicated by tcl analysis.

EXAMPLE 16

A mixture of 3.0 g of 19-hydroxy-17β-pivaloxyandrosta-4,6,8(14)-trien-3-one, 2.7 l of carbon tetrachloride and 2.4 g of meta-chloroperbenzoic acid was left to stand for 2 days at room temperature whereupon it was extracted three times with 100 ml of 2% aqueous potassium hydroxide followed by one extraction with 100 ml of water. Drying with sodium sulfate followed by evaporation at reduced pressure gave a foam. Treatment of the foam with hexane gave a waxy solid which was collected by filtration. After drying at high vacuum 2.48 g of a product was obtained which contained 14α-hydroxy-8,19-oxido-17β-pivaloxyandrosta-4,6-dien-3-one as a by-product and consisted mainly of 19-hydroxy-8β,,14β-oxido-17β-pivaloxyandrosta-4,6-dien-3-one. The latter product was then treated with 2.48 ml of acetic anhydride and 5.96 ml of pyridine for 16 hours at room temperature under nitrogen whereupon 168.8 ml of water was added and the mixture was extracted with 2 volumes of ether. The ethereal phase was extracted four times with water and then evaporated at reduced pressure. The residue obtained was treated with hexane-ether and the precipitate consisting essentially of 14α-hydroxy-8,19-oxido-17β-pivaloxyandrosta-4,6-dien-3-one was filtered off. The mother liquor was filtered through diatomaceous earth and concentrated at reduced pressure. Filtration gave 19-actoxy-8β,14β-oxido-17β-pivaloxyandrosta-4,6-dien-3-one, uv max 286 mμ.

EXAMPLE 17

A mixture of 50 mg of 19-acetoxy-8β,14β-oxido-17β-pivaloxyandrosta-4,6-dien-3-one and 0.5 ml of methanol was cooled in an ice-bath whereupon 5 mg of sodium borohydride was added. After 25 minutes 5 volumes of water were added and the mixture was extracted with ether. Evaporation of the ethereal phase at reduced pressure gave a foam consisting essentially of 19-acetoxy-3β-hydroxy-8β,14β-oxido-17β-pivaloxyandrosta-4,6-diene, uv max 254 mμ. The product was then left to stand with 0.05 ml of acetic anhydride and 0.1 ml of pyridine and nitrogen for 16 hours whereupon water was added and the mixture was extracted with ether. Extraction of the ethereal phase with water followed by evaporation and recrystallization of the residue with methanol gave 18.7 mg of 3β,19-diacetoxy-8β,14β-oxido-17β-pivaloxyandrosta-4,6-diene, uv max 245 mμ, ir max (KBr) 1742, 1727, 1724, 1370, 1248, 1158 and 1040 cm$^{-1}$.

EXAMPLE 18

A mixture of 15 mg of 3β,19-diacetoxy8β,14β-oxido-17β-Pivaloxyandrosta-4,6-diene, 6 mg of 5% palladium on charcoal and 0.9 ml of acetic acid was shaken in an atmosphere of hydrogen at room temperature for 15 minutes whereupon 9 ml of ether was added and the mixture was filtered through diatomaceous earth. The filterate was evaporated at reduced pressure and the residue obtained, together with 0.9 ml of acetic acid-ethyl acetate 1:10 and 6 mg of 5% palladium on charcoal, was agitated in an atmosphere of hydrogen at room temperature for 3 days whereupon it was diluted with 10 volumes of ether and filtered through diatomaceous earth. The filtrate was evaporated at reduced pressure and the resinous substance obtained was chromatographed on a thick layer plate coated with silica gel. Elution with ethyl acetate-benzene 1:4 gave a fraction which after recrystallization from ether-hexane yielded 3β,19-diacetoxy-14β-hydroxy-17β-pivaloxy-5α-androst-7-ene as evidenced by comparison of the infra red spectrum of the product with the infra red spectrum of the product obtained in Example 4.

EXAMPLE 19

A mixture of 2 mg of 3β,19-diacetoxy-8β,14β-oxido-17β-pivaloxyandrosta-4,6-diene, 0.12 ml of ethyl acetate and 0.8 mg of 5% palladium on charcoal was agitated in an atmosphere of hydrogen for 16 hours whereupon 10 volumes of ether were added and the mixture was filtered through diatomaceous earth. Evaporation at reduced pressure gave a product which consisted of 3β,19-diacetoxy-8β,14β-oxido-17β-pivaloxy-5α-androstane and 3β,19-diacetoxy-14β-hydroxy-17β-pivaloxy-5α-androst-7ene as indicated by tlc analysis.

EXAMPLE 20

A mixture of 80 mg of 19-acetoxy-8β,14β-oxido-17β-pivaloxyandrosta-4,6-diene-3-one and 0.8 ml of 0.2 N methanolic potassium hydroxide was left to stand at room temperature under nitrogen for 1 hour whereupon it was neutralized with a 0.2 N solution of acetic acid in ethyl acetate. The mixture was evaporated at reduced pressure, ether was added followed by charcoal and the suspension was filtered through diatomaceous earth. Concentration of the filtrate gave 51 mg of a precipitate which was recrystallized from ether-petroleum-ether yielding 19-hydroxy-8β,14β-oxido-17β-pivaloxyandrosta-4,6-dien-3-one, mp 145°–147° C, ir max (KBr) 3450–3480, 1725, 1665, 1170 and 1160 cm$^{-1}$.

EXAMPLE 21

A mixture of 200 mg of 19-hydroxy-17β-pivaloxyandrosta-4,6,8(14)-trien-3-one, 100 ml of hexane and 50 mg of metachloroperbenzoic acid was refluxed for 30 minutes, whereupon a second lot of 50 mg of metachloroperbenzoic acid was added. After 75 minutes of refluxing a third lot of 50 mg of metachloroperbenzoic acid was added. After 90 minutes of refluxing the mixture was cooled to room temperature and then extracted three times with 2% potassium hydroxide and evaporated yielding 19-hydroxy-8β,14β-oxido-17β-pivaloxyandrosta,4,6-dien-3-one, uv max 286 mμ, as the major product as indicated by comparison of its tlc chromatogram with that of the intermediate product prepared according to the epoxidation procedure of Example 16.

EXAMPLE 22

To a mixture of 250 mg of 19-hydroxy-8β,14β-oxido-17β-pivaloxyandrosta-4,6-dien-3-one and 2.5 ml of methanol, which was cooled by a methanol-ice bath below 0° C, was added 50 mg of sodium borohydride with stirring. Five minutes after the addition of the sodium borohydride uv analysis showed the reaction to be complete, and 15 ml of water was added. The precipitate which had formed was filtered, dried and then recrystallized from ether-petroleum ether yielding 3β,19-dihydroxy-8β,14β-oxido-17β-pivaloxyandrosta-4,6-diene, mp 131–132° C, uv max mμ.

EXAMPLE 23

A mixture of 5 mg of 19-acetoxy-8β,14β-oxido-17β-pivaloxyandrosta-4,6-dien-3-one, 0.5 ml of ether and 0.5 ml of a solution of 1 part of concentrated hydrochloric acid in 100 parts of ether was left to stand at room temperature for 75 minutes whereupon it was extracted with 2% aqueous potassium hydroxide and then by water. Evaporation at reduced pressure gave a material considered to be 19-acetoxy-14β-hydroxy-17β-pivaloxyandrosta-4,6,8(9)-trien-3-one, which by tlc was more polar than the starting material and which had uv max 239 (major peak), 288 (minor peak) and 357 (medium peak) mμ.

EXAMPLE 24

A mixture of 20 mg of 19-acetoxy-8β,14β-oxido-17β-pivaloxyandrosta-4,6-dien-3-one, 0.2 ml of methanol and 0.2 ml of a solution of one part of concentrated hydrochloric acid and 200 parts of methanol was left to stand at room temperature under nitrogen for 25 minutes whereupon it was neutralized by addition of sodium bicarbonate. Concentration followed by dilution with water and extraction with ether gave after evaporation of the ethereal phase a material which by uv spectroscopy and by tlc was identical to the material obtained in Example 23.

EXAMPLE 25

A mixture of 50 mg of 19-hydroxy-20β-pivaloxyandrosta-4,6,8(14)-trien-3-one, 50 ml of carbon tetrachloride and 40 mg of meta-chloroperbenzoic acid was left to stand in the dark at room temperature under nitrogen for 1 day whereupon undissolved starting material was removed by filtration. The filtrate was extracted three times with 20 ml of 2% aqueous potassium hydroxide and then once with water. Concentration at reduced pressure followed by filtration yielded 19-hydroxy-8β,14β-oxido-20β-pivaloxyandrosta-4,6-dien-3-one, uv max 287 mμ.

EXAMPLE 26

To a mixture which was heated to 65° C and consisted of 300 mg of 3β,17β-diacetoxy-8,19-oxidoandrost-14-ene, 30 ml of glacial acetic acid and 7.5 ml of water was added 9 g of zinc powder in small lots during five hours. The mixture was then filtered and the filtrate was evaporated at reduced pressure in presence of benzene. The residue was treated with 60 ml of water and 120 ml of ether. The ethereal phase was washed with water and evaporated. The residue was dissolved in ether, petroleum ether was added and the mixture was concentrated at reduced pressure to yield, after decantation of the supernatant liquid a resinous material consisting essentially of 3β,17β-diacetoxy-19-hydroxyandrost-14-ene as evidenced by tlc. This material was used as the starting material in Example 27. Tlc analysis of the material obtained after evaporation of the supernatant liquid indicated the presence of 3β,17β,19-triacetoxy-5α-androst-14-ene.

EXAMPLE 27

A mixture of 170 mg of 3β,17β-diacetoxy-19-hydroxyandrost-14-ene, the product of Example 26, 170 ml of carbon tetrachloride and 170 mg of meta-chloroperbenzoic acid was left to stand at +5° C. under nitrogen for 20 hours whereupon it was extracted three times with 25 ml of 2% aqueous potassium hydroxide, dried with sodium sulfate and evaporated at reduced pressure. Recrystallization from methanol-methylene chloride gave 3β,17β-diacetoxy-19-hydroxy-14α,15α-oxido-5α-androstane, mp 174.5° – 175° C.

EXAMPLE 28

A mixture of 5 mg of 3β,17β-diacetoxy-19-hydroxy-14α,15α-oxido-5α-androstane, 0.01 ml of acetic anhydride and 0.02 ml of pyridine was left to stand under nitrogen for 18 hours at room temperature whereupon 0.3 ml of water was added and the mixture was extracted with 0.6 ml of ether. The ethereal phase was extracted with water and then evaporated yielding 3β,17β,19-triacetoxy-14α,15α-oxido-5α-androstane as evidenced by tlc comparison with a sample of the product prepared as described in Example 31.

EXAMPLE 29

To a mixture, which was heated to 75° C and consisted of 3β,17β-diacetoxy-8,19-oxido-5α-androst-14-ene and 10 ml of glacial acetic acid, was added one g of zinc dust with stirring. After 20 hours the organic phase was separated from the zinc dust and diluted with water. Extraction with ether followed by evaporation gave a product containing 3β,17β,19-triacetoxy-5α-androst-14-ene as a major product besides 3β,17β-diacetoxy-19-hydroxy-5α-androst-14-ene and possibly some starting material as evidenced by tlc analysis. Treatment of the residue with petroleum ether followed by decantation and evaporation of the supernatant liquid gave a product in which the triacetate was enriched. A mixture of the latter product and 2 ml of 0.2 N methanolic potassium hydroxide was then heated in a stoppered flask under nitrogen at 70° C for 16 hours during which time most of the methanol had evaporated. Addition of 2 ml 0.2 N acetic acid in ethyl acetate followed by evaporation and treatment of the residue obtained with 0.5 ml of water gave a precipitate which was digested with ethyl acetate to yield, after filtration, 3β,17β,19-trihydroxy-5α-androst-14-ene, ir max (KBr) 3390, 1455, 1060, 1030, 1008, 990 and 995 cm$^{-1}$.

EXAMPLE 30

A mixture of 22 mg of 3β,17β,19-trihydroxy-5α-androst-14-ene, 0.33 ml of pyridine and 0.165 ml of acetic anhydride was left to stand under nitrogen for 19 hours at room temperature whereupon 5 ml of water was added. The mixture was extracted with 10 ml of ether. The ethereal phase was extracted with water and evaporated at reduced pressure to yield 3β,17β,19-triacetoxy-5α-androst-14-ene which was used in the reaction described in the subsequent experiment.

EXAMPLE 31

A mixture of 17 mg of the triacetate described in Example 30, 16 ml of carbon tetrachloride and 17 mg of metachloroperbenzoic acid was left to stand under nitrogen at room temperature for 5 hours, whereupon it was extracted three times with 1.5 ml of 2% aqueous potassium hydroxide and then evaporated at reduced pressure. Tlc analysis showed that the product obtained was identical to 3β,17β,19-triacetoxy-14α,15α-oxido-5α-androstane obtained according to the procedure of Example 28.

EXAMPLE 32

To a mixture, which was heated to 75° C and consisted of 100 mg of 3β,17β-diacetoxy-8,19-oxido-5α-androst-14-ene, 5 ml of acetic acid was added 1.7 g of zinc dust during 44 hours. The mixture was then evaporated, the residue obtained was treated with 20 ml of water. The resulting emulsion was extracted with 40 ml of ether. The ethereal extract was washed with water and evaporated at reduced pressure yielding a product containing mainly 3β,17β,19-triacetoxy-5α-androst-14-ene as evidenced by tlc analysis.

EXAMPLE 33

A mixture of 20 mg of 3β,17β-diacetoxy-19-hydroxy-14α,15α-oxido-5α-androstane and 0.4 ml of 0.2 N methanolic potassium hydroxide was heated under nitrogen in a stoppered flask at 70° C for 18 hours during which time most of the solvent had evaporated. Addition of 0.4 ml of 0.2 N acetic acid in ethyl acetate followed by evaporation at reduced pressure, addition of 2 ml of water to the residue obtained and filtration gave a precipitate which was digested with ethyl acetate and water to yield 3β,17β,19-trihydroxy-14α,15α-oxido-5α-androstane, mp 254°–255.5° C.

EXAMPLE 34

To a solution of 140 mg of 3β,19-diacetoxy-14β-hydroxy-17β-pivaloxy-5α-androstane in 7.0 ml of pyridine was added 0.14 ml of thionyl chloride. The mixture was left to stand under nitrogen for 40 minutes whereupon it was poured into 70 ml of an ice-water mixture. Extraction with ether followed by washing of the ethereal phase with water and evaporation at reduced pressure gave 3β,19-diacetoxy-17β-pivaloxy-5α-androst-14-ene as a resinous material which was used as the starting material in the reaction described in the following example.

EXAMPLE 35

A mixture of the total product obtained in Example 34, 140 ml of carbon tetrachloride and 105 mg of metachloroperbenzoic acid was left to stand at room temperature for five hours whereupon it was extracted three times with 11.4 ml of 2% aqueous potassium hydroxide and once with 20 ml of water. Drying with sodium sulfate followed by evaporation at reduced pressure gave a residue which crystallized on treatment with petroleum ether. Filtration and subsequent recrystallization of the precipitate obtained with methanol-water gave 3β,19-diacetoxy-14α,15α-oxido-17β-pivaloxy-5α-androstane, mp 141°–143° C which was characterized and identified by ir and nmr spectroscopy.

EXAMPLE 36

A mixture of 50 mg of 3β,19-diacetoxy-17β-pivaloxy-5α-androst-14-ene and 1.0 ml of 2 N methanolic potassium hydroxide was left to stand under nitrogen at 70° C in a stoppered bottle for 16 hours during which time some of the methanol had evaporated. A solution of 1.05 ml of 2 N acetic acid in ethyl acetate was then added and the solvents were evaporated at reduced pressure. Treatment of the residue obtained with water filtration and digestion of the precipitate obtained with ether afforded 3β,17β,19-trihydroxy-5α-androst-14-ene, mp 210°–212° C ir max (KBr), 3370, 1455, 1065, 1030, 1008, 990 and 955 cm$^{-1}$.

EXAMPLE 37

A mixture of 54 mg of 3β,19-diacetoxy-14α-15α-oxido-17β-pivaloxy-5α-androstane and 1.08 ml of 0.2 N methanolic potassium hydroxide was left to stand under nitrogen at 70° C in a stoppered bottle for 20 hours during which time most of the methanol had evaporated. A solution of 1 ml of 0.2 N acetic acid in ethyl acetate was then added and the solvents were removed at reduced pressure. Treatment of the residue obtained with water, filtration, and digestion of the precipitate with ethyl acetate gave 14α,15α-oxido-3β,17β,19-trihydroxy-5α-androstane, mp (evacuated tube) 254°–255.5° C.

EXAMPLE 38

To a mixture which was immersed in a 65° C heating bath and consisted of 88 mg of 3β-acetoxy-8,19-oxido-17β-pivaloxy-5α-androst-14-ene, 8.8 ml of glacial acetic acid and 2.2 ml of water was added 2.64 g of zinc dust in small lots during 65 minutes. The residual zinc was then filtered off and the filtrate was evaporated at reduced pressure. The residue obtained was treated with 16 ml of water and 32 ml of ether. The ethereal phase was washed three times with 5 ml of water and then evaporated. Thick layer chromatography of the residue on silica gel gave, on elution with ethyl acetate-benzene 1:10, 61 mg of the purified product which was recrystallized from ether-pentane to yield 47 mg of 3-acetoxy-19-hydroxy-17β-pivaloxy-5α-androst-14-ene, mp 133°–133.5° C.

EXAMPLE 39

To a solution, immersed in an oil bath heated to 58°–68° C, of 5 mg of 3β-acetoxy-8,19-oxido-20β-pivaloxy-5α-pregn-14-ene in 0.5 ml of glacial acetic acid and 0.125 ml of water was added 150 mg of zinc dust. The mixture was stirred magnetically for 3 hours using an iron nail as the stirring bar. It was then cooled and diluted with 10 volumes of water. Extraction with ether, followed by extraction of the ethereal phase with water, excess 2% aqueous potassium hydroxide, drying with sodium sulfate and evaporation at high vacuum yielded a foam consisting essentially of 3β-acetoxy-19-hydroxy-20β-pivaloxy-5α-pregn-14-ene as indicated by tlc-analysis of the product and its 19-acetate, which was prepared by the standard method using acetic anhydride and pyridine, as, for example, described in Example 47.

EXAMPLE 40

Zinc dust reduction of 7 mg of 3β,21-diacetoxy 8,19-oxido-5α-pregn-14-en-20-one when carried out by a procedure essentially the same as the one described in Example 39, gave 3β,21-diacetoxy-19-hydroxy-5α-pregn-14-en-20-one as indicated by tlc analysis.

EXAMPLE 41

Zinc dust reduction of 5 mg 21-acetoxy-3β-hydroxy-8,19-oxido-5α-pregn-14-en-20one, when carried out by a procedure essentially the same as the one described in Example 39 gave 21-acetoxy-3β,19-dihydroxy-5α-pregn-14-en-20-one as indicated by tlc analysis.

EXAMPLE 42

A mixture of 1 g. of 3β,19-dihydroxy-20β-pivaloxy-5α-pregn-8(14)-ene 900 mg of metachloroperbenzoic acid and 1000 ml of carbon tetrachloride was stirred under nitrogen in the dark. After 1 hour of stirring all solid material had dissolved. After 4 hours the solution was extracted 3 times with 200 ml of 2% aqueous potassium hydroxide, once with 400 ml of water, dried with sodium sulfate and evaporated at reduced pressure. Treatment of the residue obtained with ether-methylene chloride and pentane gave a 717 mg of a white solid consisting essentially of 3$\beta$,19-dihydroxy-8$\beta$,14$\beta$-oxido-20$\beta$-pivaloxy-5$\alpha$-pregnane, which was used as the starting material for the reaction described in Example 44. Recrystallisation with ether-hexane gave the purified crystalline product. Tlc indicated the presence of a by-product, which was considered to be 3$\beta$,14$\alpha$-hydroxy-8,19-oxido-20$\beta$-pivaloxy-5$\alpha$-pregnane.

EXAMPLE 43

A mixture of 300 mg of 3$\beta$,19-dihydroxy-8$\beta$,14$\beta$-oxido-20$\beta$-pivaloxypregnane, 2,4 ml of pyridine and 1.2 ml of acetic anhydride was left to stand under nitrogen for 20 hours at room temperature whereupon 36 ml of water was added. The resulting emulsion was extracted with 72 ml of ether and the ethereal solution was extracted three times with 20 ml of water. Evaporation at reduced pressure gave a residue, which on treatment with methanol-water 10:1 containing a trace of pyridine gave a 146.8 mg of a crystalline precipitate of 3$\beta$,19-diacetoxy-8$\beta$,14$\beta$-oxido-20$\beta$-pivaloxy pregnane, as evidenced by tlc analysis.

EXAMPLE 44

A mixture of 400 mg of 3$\beta$,19-dihydroxy-8$\beta$,14$\beta$-oxido-20$\beta$-pivaloxy-5$\alpha$-pregnane, 20 ml of glacial acetic acid and 200 mg of 5% palladium on charcoal was agitated in an atmosphere of hydrogen for 150 minutes, whereupon the hydrogen atmosphere was replaced by nitrogen, 60 ml of ether was added and the mixture was filtered through diatomaceous earth. The filtrate was cooled in an ice-bath and 80 ml of a 25% aqueous potassium hydroxide solution was added. The organic phase was washed several times with water, dried with sodium sulfate and evaporated. Chromatography of the resinous product on silica gel G coated glass plates gave, on elution with ethyl acetate-benzene 2:1, 3$\beta$,14$\beta$-dihydroxy-8,19-oxido-20$\beta$-pivaloxy-5$\alpha$-pregnane, 3$\beta$,14$\alpha$-dihydroxy-8,19-oxido-20$\beta$-pivaloxy-5$\alpha$-pregnane and 3$\beta$,14$\beta$,19-trihydroxy-20$\beta$-pivaloxy-5$\alpha$-pregn-7-ene, as evidenced by tlc analysis and chemical transformations of the first and third product.

EXAMPLE 45

A mixture of 2 mg of 3$\beta$,14$\beta$,19-trihydroxy-20$\beta$-pivaloxy-5$\alpha$-pregn-7-ene, 0.032 ml of pyridine and 0.016 ml of acetic anhydride was left to stand at room temperature under nitrogen for 18 hours, whereupon 0.5 ml of water was added. Extraction with 1 ml of ether followed by evaporation at reduced pressure gave 3$\beta$,19-diacetoxy-14$\beta$-hydroxy-20$\beta$-pivaloxy-5$\alpha$-pregn-7-ene as evidenced by tlc analysis.

EXAMPLE 46

A mixture of 40 mg of 3$\beta$,19-dihydroxy-8$\beta$,14$\beta$-oxido-17$\beta$-pivaloxy-5$\alpha$-androstane, 20 mg of 5% palladium on charcoal and 4 ml of glacial acetic acid was agitated at room temprature in an atmosphere of hydrogen for 150 minutes, whereupon 30 ml of ether was added and the mixture was filtered through diatomaceous earth under nitrogen. The filtrate was cooled by a bath of cold water and 10 ml of 50% aqueous potassium hydroxide was added. The organic phase was extracted 3 times with water, dried with sodium sulfate and evaporated. The resinous product obtained was chromatographed on silica gel G coated glass plates. Elution with ethyl acetate-benzene gave 2 fractions. Treatment of the less polar fraction with hexanemethanol gave a crystalline solid of 3$\beta$,14$\beta$-dihydroxy-8,19-oxido-17$\beta$-pivaloxy-5$\alpha$-androst-7-ene. Acetylation of these products with acetic anhydride and pyridine under standard conditions, as for example described in Example 45, gave 3$\beta$-acetoxy, 14$\beta$-hydroxy-8,19-oxido-17$\beta$-pivaloxy-5$\alpha$-androstane and 3$\beta$,19-diacetoxy-14$\beta$-hydroxy-17$\beta$-pivaloxy-5$\alpha$-androst-7-ene, as evidenced by tlc analysis and their respective ir-spectra.

EXAMPLE 47

A mixture of 20 mg of 19-hydroxy-8$\beta$,14$\beta$-oxido-20$\beta$-pivaloxy-pregna-4,6-dien-3-one, 0.08 ml of pyridine and 0.04 ml of acetic anhydride was left to stand at room temperature under nitrogen for 16 hours, whereupon 2.4 ml of water was added. The mixture was extracted with 4.8 ml of ether, the ethereal phase was extracted 3 times with water and evaporated yielding a resin which solidified on treatment with pentane-hexane. Recrystallisation from pentane-hexane gave 6.2 mg of 19-acetoxy-8$\beta$,14$\beta$-oxido-20$\beta$-pivaloxy-pregna-4,6-dien-3-one, mp 161°–163°, as evidenced by tlc analysis and ir-spectroscopy.

EXAMPLE 48

To a mixture, immersed in an oil-bath heated to 65° C, of 100 mg of 3-hydroxy-8,19-oxido-5$\alpha$-pregn-14-en-20-one tetrahydropyranyl ether and 12.5 ml of glacial acetic acid-water 4:1, was added 1.5 g of zinc dust. The mixture was stirred mechanically for 1½ hours whereupon another 1.5 g of zinc was added. The mixture was then stirred for another hour at the same temperature. Filtration, followed by addition of water to the filtrate, azeotropic distillation at reduced pressure, extraction of the aqueous mixture with methylene chloride, drying with sodium sulfate, addition of hexane, -dihydroxy-at reduced pressure and filtration gave 53 mg of a white precipitate consisting of 3$\beta$,19-dihydroxy-5$\alpha$-pregn-14-en-20-one as indicated by tlc analysis of the product and its 3,19-diacetate.

EXAMPLE 49

To a mixture, immersed in an oil bath heated to 70°, of 50 mg of 3$\beta$-acetoxy-8,19-oxido-5$\alpha$-pregn-14-en-20-one, 5.0 ml of glacial acetic acid and 1.25 ml of water was added 750 mg of zinc dust with stirring. After 130 minutes of stirring an additional lot of 375 mg of zinc dust was added. Stirring was continued for one hour whereupon water was added and the mixture was evaporated at reduced pressure. The residue was treated with water and extracted with ether. Treatment of the residue with pentane, followed by filtration gave 13.6 mg of 3$\beta$-acetoxy-19-hydroxy-5$\alpha$-pregna-14-en-20-one, as a white solid, ir (nujol) 3510, 1730, 1695, 1250, 1203, 1035, 978 and 960 cm$^{-1}$.

EXAMPLE 50

A mixture of 900 mg of 3$\beta$-acetoxy-8,19-oxido-5$\alpha$-pregn-14-en-20-one, 67.5 ml of toluene, 22.5 ml of 90% formic acid and 27 g of zinc dust was stirred for 90 minutes whereupon a sample of the clear supernatant liquid was withdrawn and evaporated. TLC analysis of the material obtained showed that the major steroid in the sample was 3β-acetoxy-19-hydroxy-5α-pregn-14-en-20-one. After 31 hours of stirring the mixture was stored at +5° for 18 hours. The clear supernatant liquid was then extracted by addition of benzene, agitation and decantation. The residue was further extracted by addition of ethyl acetate-water and filtration. Evaporation of the organic phases, followed by dissolution in methylene chloride, addition of pentane until the solution became slightly turbid, filtration through celite, concentration of the filtrate with intermittant addition of hexane and filtration gave 901 mg of 3β,19-dihydroxy-5α-pregn-14-en-20-one 3-acetate 19-formate, mp 169.5° – 171.5° C.

EXAMPLE 51

Treatment of 1.0 g of 3β-acetoxy-8,19-oxido-20β-pivaloxy-5α-pregn-14-ene with zinc, toluene and formic acid for 45 hours under conditions which were very similar to the ones described in the preceding Example gave 925 mg of 3β,19,20β-trihydroxy-5α-pregn-14-ene 3-acetate 19-formate 20-pivalate, mp 126.5° – 128°; ir max 3070 (14-ene), 1725, 1712, 1470, 1452, 1362, 1355, 1271, 1235, 1170, 1160, 1051, 1021, 960, 895, 800, 792 and 765 cm$^{-1}$.

EXAMPLE 52

A mixture of 400 mg of 3β,19,20β-trihydroxy-5α-pregn-14-ene 3-acetate 19-formate 20-pivalate, 16 ml of acetone and 8 ml of a freshly prepared solution of N-bromoacetamide in water 6:100 (g/ml) was stirred under nitrogen in absence of light in an ice-bath for 75 minutes, whereupon a solution, consisting of 240 ml of ice-water and 4 ml of saturated sodium bisulfite, was added. The resulting suspension was stirred in an ice-bath for 30 minutes and was then filtered yielding 3β,14β,19,20β-tetrahydroxy-15α-bromo-5α-pregnane 3-acetate 19-formate 20-pivalate as a white solid, which was converted to the corresponding 14β,15β-epoxide as described in the following Example.

EXAMPLE 53

A mixture of the still wet precipitate of bromohydrin obtained in the preceding Example, 2.2 ml of methylene chloride and 8.0 ml of t-butylamine was left to stand in the dark for 90 minutes whereupon the methylene chloride and t-butylamine were evaporated at reduced pressure. Addition of water, methylene chloride and hexane, concentration at reduced pressure, intermittant addition of hexane and filtration yield 311 mg of 3β,19,20β-trihydroxy-14β,15β-oxido-5α-pregnane 3-acetate 19-formate 20-pivalate.

EXAMPLE 54

A solution of 3β,14β,19-20β-tetrahydroxy-15α-bromo-5α-pregnane, which had been freshly prepared from 200 mg of 3β,19,20β-trihydroxy-5α-pregn-14-ene 3-acetate 19-formate 20-pivalate, in 26.6 ml of methylene chloride was added to a mixture of Raney-nickel, which had been freshly prepared from 12.0 g of nickel-aluminum alloy and 10% aqueous potassium hydroxide, of 4.0 ml of pivalic acid-methylene chloride 1:10 and of 80 ml of water, was shaken in an atmosphere of hydrogen for 42 hours, whereupon 100 ml of ether-methylene chloride 4:1 was added and the mixture was filtered through diatomaceous earth. The filtrate was extracted twice with ¼ volume of half-saturated aqueous sodium bicarbonate, dried with sodium sulfate and evaporated. In an effort to convert residual bromohydrin in to the more stable corresponding 14β,15β-oxide the product was then left to stand under nitrogen with 2.0 ml of tertiary butylamine, whereupon the latter was removed at reduced pressure. In an effort to remove a by-product the mixture was then dissolved in 10 ml of ethyl acetate and shaken in an atmosphere of hydrogen in presence of 100 mg of 5% palladium on charcoal at room temperature for 16 hours, whereupon 60 ml of ether-methylene chloride 4:1 was added and the mixture was filtered through celite. Evaporation of the solvents at reduced pressure followed by chromatography on silica gel G covered glass-plates gave, on elution unto ethyl acetate-benzene 1:4, 68.5 mg of 3β,14,19,20β-tetrahydroxy-5α-pregnane 3-acetate 19-formate 20-pivalate, mp 143.5° – 145.5° C, ir (KBr) 3495, 2960, 2890, 1718, 1708, 1475, 1450, 1390, 1380, 1362, 1278, 1174, 1150, 1130, 1090, 1080, 1030, 968, 995, 935, 906, 865, 815 and 770 cm$^{-1}$, and 41.5 mg of 3β,19,20β-trihydroxy-14β,15β-oxido-5α-pregnane 3-acetate 19-formate 20-pivalate, mp 173° – 176° C (clear at 181° C). Both compounds were also characterized by their mass-spectra.

EXAMPLE 55

A mixture of 200 mg of 3β,19,20β-triacetoxy-5α-pregn-14-ene, 8.0 ml of acetone, 4.0 ml of a freshly prepared solution of 300 mg of N-bromoacetamide in 5 ml of water was stirred under nitrogen in the dark in an ice-bath for 75 minutes, whereupon 8.0 ml of a half saturated solution of sodium bisulfite was added. The mixture was extracted with methylene chloride 5 times, the combined methylene chloride solutions were extracted with water, dried with sodium sulfate and evaporated at reduced pressure yielding a resin consisting of 3β,14β,19,20β-tetrahydroxy-15α-bromo-5α-pregnane 3,19,20-triacetate. A fraction (3/8) of the above product was then left to stand with 1 ml of tertiary butylamine for 30 min. in the dark under nitrogen, whereupon it was evaporated at reduced pressure. Chromatography of the product obtained on silica gel G coated glass plates gave, on elution with ethyl acetate-benzene 1:7, a fraction which after recrystallization with ether-pentane afforded 15 mg of 3β,19,20β-triacetoxy-14β,15β-oxido-5α-pregnane.

EXAMPLE 56

A mixture of 230 mg of 3β,19-dihydroxy-20β-pivaloxy-5α-pregn-14-ene and 2.76 ml of pyridine was protected by an atmosphere of nitrogen and 2.76 ml of acetic-formic anhydride was added. The mixture became warm after the addition of the reagent and was cooled externally in ice-cold water for 5 minutes. It was then left to stand under nitrogen for 125 minutes whereupon excess reagent was destroyed by addition of 10 volumes of ice-water. After standing at −5° under nitrogen the mixture was filtered yielding 241 mg of 3β,19,20β-trihydroxy-5α-pregn-14-ene 3,19-diformate 20-pivalate as a white solid.

EXAMPLE 57

To a mixture of 40 mg of 3β,19,21-triacetoxy-5α-pregn-14-en-20-one and 0.8 ml of methanol was added 0.2 ml of 2% aqueous-potassium hydroxide-methanol 1:10. The mixture was stirred under nitrogen for 50 minutes, whereupon 0.02 ml of a 2% solution of acetic acid in ethyl acetate was added. The mixture was evaporated at reduced pressure with intermittent addition of ethyl acetate. Treatment with ether, extraction with water, drying with sodium sulfate, addition of hexane until the solution became slightly turbid, filtration through diatomaceous earth and evaporation of the filtrate gave 23 mg of a product consisting mainly of 3β,19-diacetoxy-21-hydroxy-5α-pregn-14-en-20-one, as evidenced by tlc-analysis and subsequent chemical transformations.

EXAMPLE 58

A mixture of 16 mg of 3β,14β,19,20β-tetrahydroxy-5α-pregnane 3-acetate 19-formate 20-pivalate, 1.6 ml of methanol and concentrated aqueous ammonium hydroxide-water 1:10 was left to stand at −5° C for over 24 hours. Evaporation at reduced pressure, followed by chromatography on silica gel G coated glass-plates gave, on elution with ethyl acetate benzene 1:2, 7.5 mg of 3β-acetoxy-14β,19-dihydroxy-20β-pivaloxy-5α-pregnane as a white solid.

EXAMPLE 59

To a mixture of 0.180 ml of carbon tetrachloride; 0.030 ml of tertiary butanol and 3 mg of 3β-acetoxy-14β,19-dihydroxy-20β-pivaloxy-5α-pregnane was added 0.018 ml of an approximately 30% solution of tertiary butyl chromate in carbon tetrachloride. The mixture was shaken for 2 hours under nitrogen whereupon 0.18 ml of methanol was added. Dilution with 10 volumes of ether, followed by two extractions with half-saturated aqueous sodium bisulfite solution, two extractions with 2N aqueous sodium carbonate solution and evaporation of the organic phase gave 3β-acetoxy-14β-hydroxy-20β-pivaloxy-5α-pregnane-19-al as evidenced by tlc-analysis.

EXAMPLE 60

A mixture of 0.07 ml of pyridine and 7.0 mg of chromium trioxide was stirred under nitrogen for 45 minutes with external cooling by an ice-bath, whereupon a solution of 5 mg of 3β-acetoxy-19-hydroxy-20β-pivaloxy-5α-pregn-14-ene in 0.17 ml of pyridine was added. Stirring was continued without external cooling for approximately 5 hours whereupon 0.093 ml of isopropanol was added. The mixture was stirred for a further 5 minutes and was then evaporated at reduced pressure. Treatment of the residue obtained with ether, followed by filtration and evaporation gave 3β-acetoxy-20β-pivaloxy-5α-pregn-14-en-19-al as evidenced by tlc-analysis.

EXAMPLE 61

A mixture of approximately 8 mg of 15β-bromo-3β,19-diacetoxy-14β-hydroxy-20β-pivaloxy-5α-pregnane, 0.8 ml of dry ether, 0.8 ml of dry tetrahydrofuran and 80 mg of lithium aluminium hydride was left to react under nitrogen at approximately −70° C for 30 minutes and then at approximately 0° C for 30 minutes by appropriate external cooling. A sample subsequently withdrawn was treated with wet ether and water. Tlc-analysis of the sample showed the presence of 14β,15β-oxido-3β,19,20β-trihydroxy-5α-pregnane as practically the only steroidal product. The mixture was shaken at room temperature for 3 days and then treated with wet ether and water and evaporated at reduced pressure. Tlc-analysis of the material obtained showed the presence of 3β,14β,19,20β-tetrahydroxy-5α-pregnane as practically the only steroidal product.

EXAMPLE 62

Treatment of 3β,19-diacetoxy-14β,15β-oxido-20β-pivaloxy-5α-pregnane with lithium aluminium hydride as described in the preceding Example gave similarly 3β,14β,19,20β-tetrahydroxy-5α-pregnane via 14β,15β-oxido-3β,19,20β-trihydroxy-5α-pregnane.

EXAMPLE 63

When 20 mg of 3β,19-diacetoxy 8β,14β-oxido-20β-pivaloxy-5α-pregnane were treated with lithium aluminium hydride for 3 days similarly as described in the preceding Example 8β,14β-oxido-3β,19,20β-trihydroxy-5αpregnane was obtained as evidenced by tlc-analysis.

EXAMPLE 64

A mixture of 275 mg of 3β-acetoxy-19-formyloxy-14β,15β-oxido-20β-pivaloxy-5α-pregnane, 55 ml of dry tetrahydrofuran and 550 mg of lithium aluminium hydride was shaken under nitrogen at room temperature for 3 days, whereupon 60 ml of wet ether was added with external cooling, followed by 6 ml of water. The mixture was then shaken for 1.5 hours and the volatile material was evaporated at reduced pressure. The resulting white solid was stirred with ethyl acetate-methanol 1:1 for 1 hour. The mixture was filtered and the filtrate was evaporated yielding a solid containing 3β,14β,19,20β-tetrahydroxy-5α-pregnane as the major steroid, as evidenced by thin layer chromatography. The latter material, 9.9 ml of pyridine and 4.95 ml of acetic anhydride was left to stand under nitrogen overnight. The solid material which had then separated was scraped loose and the mixture was magnetically stirred under nitrogen overnight, whereupon 15 ml of benzene-methylene chloride 4:1 was added. The mixture was filtered and the filtrate was evaporated at reduced pressure yielding 270 mg of a product consisting essentially of 3β,19,20β-triacetoxy-14β-hydroxy-5α-pregnane as evidenced by thin layer chromatography.

A mixture of 107 mg of the latter product, 5.35 ml of anhydrous dimethylformamide and 96.2 mg of sodium hydride was then shaken under nitrogen for 20 hours, whereupon the reaction mixture was added slowly to 20 ml of wet ether. The mixture was then treated with 0.5 ml of water and 0.3 ml of acetic acid-water 1:2. The organic phase was evaporated at reduced pressure and chromatographed on silica gel G coated glass plates, using ethyl acetate benzene 1:1 as the eluant. The less polar fraction isolated consisted in part of 3β,19-diacetoxy-14β,20β-dihydroxy-5α-pregnane, as evidenced by tlc-analysis and mass-spectroscopy; m/e 434 (m-2) 418 (m-18), 416 (m-2-18), 374 (m-2-60) and 358 (m-60-18). The mass-spectroscopy also indicates the presence of another product having a molecular weight which is lower by two units. The more polar fraction contained 19-acetoxy-3β,14β,20β-trihydroxy-5α-pregnane as evidenced by tlc-analysis.

EXAMPLE 65

A mixture of 30 mg of the 3,14,20-triacetate described in Example 64, 1.5 ml of t-butylamine and 0.375 ml of water was shaken under nitrogen overnight whereupon 0.375 ml of water was added. The mixture was shaken for 24 hours and an additional lot of 0.375 ml of water was added. The mixture was shaken for another 24 hours and was then evaporated at reduced pressure. Chromatography of the resinous residue on silica gel G coated glass plates with ethyl acetate benzene 1:2 as the eluant gave 8.7 mg of a resin consisting essentially of 19,20-diacetoxy-3β,14β-dihydroxy-5α-pregnane.

The latter product, 0.174 ml of pyridine and 0.0348 ml of pivaloyl chloride were left to stand under nitrogen for 20 hours, whereupon 2.18 ml of water was added. Extraction of the reaction mixture with ether-methylene chloride 4:1, extraction of the organic phase with water, half-saturated sodium bicarbonate and water, drying with sodium sulfate and evaporation at reduced pressure, followed by recrystallisation of the yellow solid obtained with ether-pentane gave 7 mg of 19,20β-diacetoxy-14β-hydroxy-3β-pivaloxy-5α-pregnane, mp 106°–109° C, m/e 502(m-18, 460, 445, 442, 439, 431, 427, 416, 413, 400, 392, 382, 379, 369 and 358.

EXAMPLE 66

To 0.414 ml of t-butanol, which was stirred under nitrogen, was added 4.14 mg of lithium aluminium hydride. The mixture was stirred for one hour whereafter 13 mg of the 3,19,20-triacetate, described in Example 64, was added. The mixture was further stirred for 23 hours, was then cooled till it partially froze and 0.27 ml of acetic acid-ether 1:10 was added in one lot. Subsequent addition of wet ether, followed by evaporation at reduced pressure with intermittant addition of toluent and chromatography of the residue obtained on silica gel G coated glass plates with ethyl acetate-benzene 1:1 as the eluant, gave a fraction which, after recrystallisation from ether-hexane yielded 2.69 mg of 3β,20β-diacetoxy-14β,19-dihydroxy-5α-pregnane, mp 180, 182°–183° C., m/e 418 (m-18), 385, 376, 358, 344, 327, 316, 298 and 283 as evidenced also by tlc-analysis. A further fraction which was isolated was more polar and was considered to consist of the isomeric 19,20β-diacetoxy-3β,14β-dihydroxy-5α-pregnane.

EXAMPLE 67

Treatment of 150 mg of 8,19-oxido-20β-pivaloxy-5α-pregn-14-ene under conditions similar to those described in Example 50 gave approximately 130 mg of 19-formyloxy-20β-pivaloxy-5α-pregn-14-ene as a glassy resin after dissolution of the crude reaction product in methylene chloride, addition of hexane till a faint turbidity appeared, filtration through diatomaceous earth and evaporation of the filtrate at reduced pressure.

EXAMPLE 68

Treatment of 110 mg of the product of the preceding Example under conditions essentially the same as those described in Example 52 gave a white precipitate of 15α-bromo-14β-hydroxy-19-formyloxy-20β-pivaloxy-5αpregnane after addition of the aqueous sodium bisulfite and water to the reaction mixture.

The above bromohydrin when treated under conditions essentially the same as those described in Example 53, except that as the co-solvent ether-methylene chloride 4:1 instead of methylene chloride was being used, gave, after evaporation at reduced pressure and recrystallisation of the residue obtained with methanol-water 8:1.6, 92 mg of 19-formyloxy-14β,15β-oxido-20β-pivaloxy-5α-pregnane.

Reduction of 75 mg of the latter oxide with lithium aluminium hydride under conditions similar to those described in Example 64 gave, after the decomposition of the excess reagent with wet ether, water and evaporation, at reduced pressure, a white residue which was digested with ethyl acetatemethanol 10:1. Subsequent filtration through diatomaceous earth, evaporation of the filtrate, treatment of the residue obtained in methylene chloride, filtration, concentration of the filtrate at reduced pressure with intermittant addition of ether and filtration gave 39.3 mg of a product consisting mainly of 14β,19,20β-trihydroxy-5α-pregnane as a gelatinous precipitate, m/e 336 (m), 334, 318 (strong), 316 (medium), 300 (strong), 298 (weak), 287 (very strong; m-31-18), as also evidenced by tlc-analysis.

EXAMPLE 69

Treatment of 2 mg of 8,19-oxido-5α-androst-14en-17β-carboxylic acid, which was obtained as described in copending patent application Ser. No. 497,729 filed Aug. 15, 1974 under conditions similar to those described in Example 50 gave 19-formyloxy-5α-androst-14-en-17β-carboxylic acid, as evidenced by tlc-analysis.

EXAMPLE 70

A mixture of 2 mg of 21-hydroxy-8,19-oxido-5α-pregn-14-en-20-one, 60 mg of zinc dust, 0.1 ml of methylene chloride and 0.2 ml of methylene chloride saturated with 90% aqueous formic acid was shaken at room temperature. Evaporation of part of the supernatant liquid after 30 minutes gave a product containing 19,21-dihydroxy-5α-pregn-14-en-20-one as the major steroidal product, as evidenced by tlc.

After 16 hours of shaking 0.3 ml of ethyl acetate and 0.15 ml of water were added and the mixture was filtered after brief shaking. Extraction of the organic phase with water followed by evaporation gave a product considered to consist mainly of a mixture of 21-formyloxy-19-hydroxy-5α-pregn-14-en-20-one and its isomeric 19-formyloxy 21-hydroxy analog as evidenced by tlc.

EXAMPLE 71

A mixture of 9 mg of 19,21-dihydroxy-5α-pregn-14-en-20-one, 0.18 ml each of pyridine and acetic-formic anhydride was left to stand at room temperature for 30 minutes, whereupon 1.18 ml of water was added and the mixture was left to stand at −5° C for one day. The white precipitate was filtered, dried and reformylated essentially as outlined above except that in the working up the excess pyridine and reagent were removed at high vacuum. Dissolution of the crystalline residue in methylene chloride-ether 1:1, addition of hexane till a faint turbidity appeared, filtration through diatomaceous earth, and concentration of the filtrate with intermittant addition of ether and hexane gave 19,21-diformyloxy-5α-pregn-14-en-20-one, mp 121, 122°–123° C., ir (KBr) 3040, 2940, 2910, 2839, 1731, 1711, 1470, 1440, 1370, 1270, 1172, 1090, 961, 948, 905, 796 and 756 cm$^{-1}$.

Treatment of 1 mg of the latter product in 0.2 ml of methanol with 0.020 ml of 10% aqueous sodium bicarbonate at room temperature for 2 hours, followed by neutralisation with 20λ of 2% glacial acetic acid in ethyl acetate and evaporation gave a product containing as the major steroidal product 21-hydroxy-19-formyloxy-5α-pregn-14-en-20-one, as evidenced by tlc analysis.

EXAMPLE 72

A mixture of 900 mg of 3β-acetoxy-8,19-oxido-20β-pivaloxy-5α-pregn-14-ene, 67.5 ml of toluene, 9.0 ml of 90% aqueous formic acid and 27.0 g of zinc dust was shaken at room temperature. After 15 minutes lumps started to form, which were broken up. After 2½ hours of total shaking time the supernatant clear liquid was decanted and the zinc sludge was washed three times with 18 ml of benzene. The supernatant liquid and the washings were evaporated at reduced pressure with intermittant addition of hexane, and the residue obtained was dissolved in ether. Addition of hexane till a turbidity appeared, followed by filtration through diatomaceous earth, concentration of the filtrate with intermittant addition of hexane and filtration of the precipitate obtained gave 584.96 mg of 3β-acetoxy-19-hydroxy-20β-pivaloxy-5α-pregn-14-ene, mp 176°–178° C. The mother liquid contained 3β-acetoxy-19-formyloxy-20β-pivaloxy-5α-pregn-14-ene, besides the latter compound, as evidenced by tlc.

I claim:

1. A compound of the formula

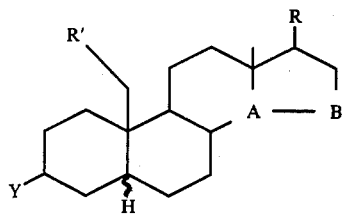

wherein R is o-pivalate or >-o-pivalate, R' is chosen from OH, O-acyl, and =O, A-B is chosen from C(β-OH)-CH$_2$; C=CH;

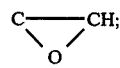

and C(β-OH)-CHBr; and Y is chosen from O-acyl, =O, OH, H and O-tetrahydropyranyl ether, wherein acyl is chosen from formyl, acetyl, trimethyl acetyl and triethyl acetyl, and the Δ4, Δ5, Δ6, Δ7, Δ8 (9) dehydro analogues thereof.

2. A compound of the formula

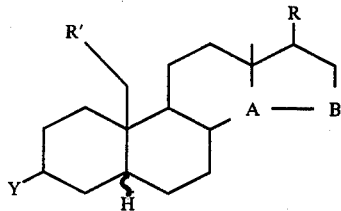

wherein R is OH or O-acyl, R' is chosen from OH and O-acyl, Y is chosen from OH, O-acyl, =O and H, A-B is chosen from C(β-OH)CH$_2$, C=CH and

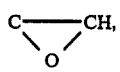

wherein acyl is formyl, acetyl, trimethyl acetal and triethyl acetyl, and the Δ4, Δ5, Δ6, Δ7, Δ8 (9) dehydro anloagues thereof.

3. A compound of the formula

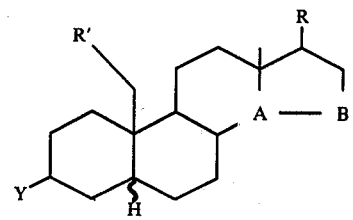

wherein R is >-OH or >-O-acyl, R' is OH or O-acyl, Y is OH, O-acyl, =O, and H, A-B is C(β-OH)-CH$_2$,

C(β-OH)-CH$_2$Br wherein acyl is chosen from formyl, acetyl, trimethyl acetyl and triethyl acetyl.

4. A compound of the formula

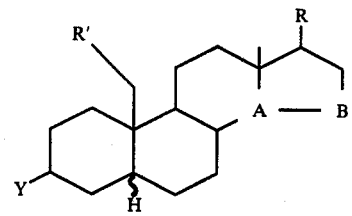

wherein R is

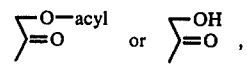

R' is OH, Y is O-acyl, OH, H, A-B is C=CH, wherein acyl is chosen from formyl, acetyl, trimethyl acetyl and triethyl acetyl.

5. A compound of the.formula

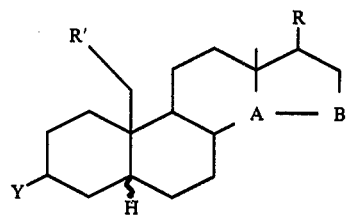

wherein R is >=O or >-OH, R' is OH or O-acyl, Y is H, OH, O-acyl, A-B is C=CH, C(β-OH)-CH$_2$ and

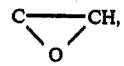

wherein acyl is chosen from formyl, acetyl, trimethyl acetyl and triethyl acetyl.

6. A compound of the formula

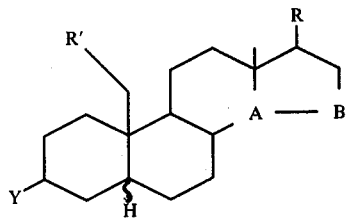

wherein R is COOH, R' is O-acyl, Y is H, A-B is C=CH, wherein acyl is chosen from formyl, acetyl, trimethyl acetyl and triethyl acetyl.

7. A compound as defined in claim 1, wherein Y is H.
8. A compound as defined in claim 1, wherein R is O-pivalate and R' is O-acyl.
9. A compound as defined in claim 8, wherein A-B is C(β-OH)-CH$_2$.
10. A compound as defined in claim 8, wherein Y is O-acyl.
11. A compound as defined in claim 1, wherein R is O-pivalate, R' is OH and A-B is C=CH.
12. A compound as defined in claim 1, wherein R is O-pivalate, R' is O-acyl and A-B is

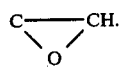

13. A compound as defined in claim 1, wherein R' >-O-pivalate and A-B is C(β-OH)-CH$_2$.
14. A compound as defined in claim 1, wherein R >-O-pivalate and R' and Y are O-acyl.
15. A compound as defined in claim 2, wherein R, R' and Y are each OH.
16. A compound as defined in claim 2, wherein R, R' and Y are each O-acyl.
17. A process of preparing a compound of the formula

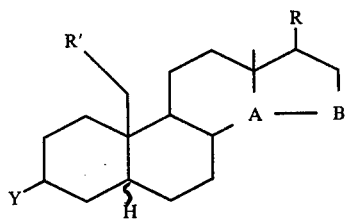

wherein R is chosen from O-pivalate, >-O-pivalate, OH, O-acyl, >-OH, >-O-acyl,

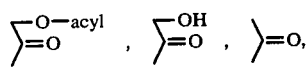

and COOH, A-B is chosen from C(β-OH)-CH$_2$, C=CH,

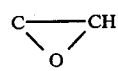

and C(β-OH)-CHBr; R' is chosen from OH, O-acyl and =O, Y is H, OH, O-acyl, =O and O-tetrahydropryranyl ether, wherein acyl is chosen from formyl, acetyl, trimethyl acetyl and triethyl acetyl, and the Δ4, Δ5, Δ6, Δ7, and Δ8(9) dehydro analogues thereof, which process is selected from the group connsisting of (a) treating a compound of the formula

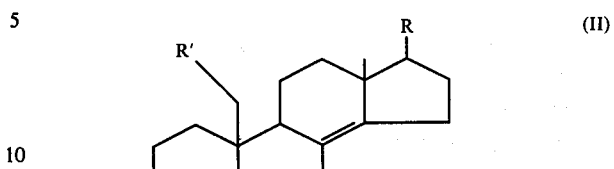

wherein R, R' and Y are as defined above, with an oxidising agent, to form a compound of the formula (III)

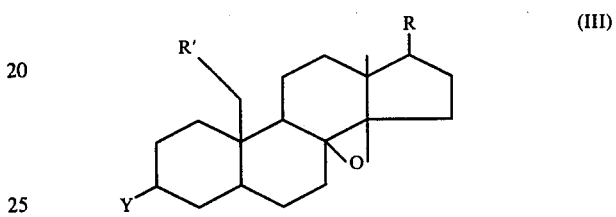

wherein R, R' and Y are as defined above, and subjecting the latter compound to a rearrangement process under hydrogenation or acidic conditions to form a compound of the formula (I) wherein the latter compound contains a 7-double bond and a 14β-hydroxy group;

(b) treating a compound of the formula

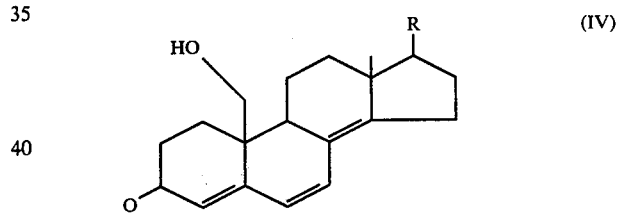

wherein R is as defined above, with an epoxidizing agent to form a compound of the formula

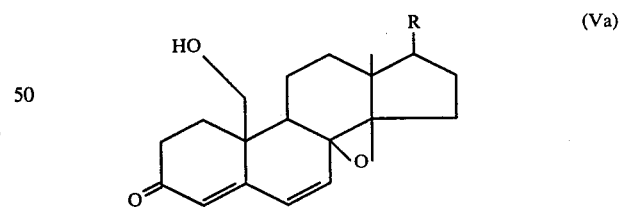

treating the latter with an acetylating agent to form a compound of the formula

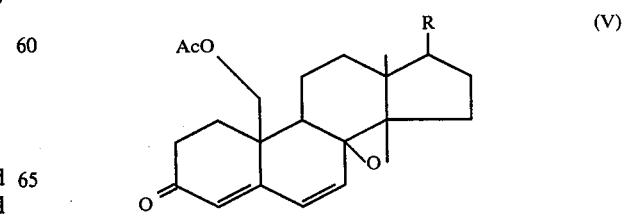

and treating the latter with an acid to form the following compound of formula I

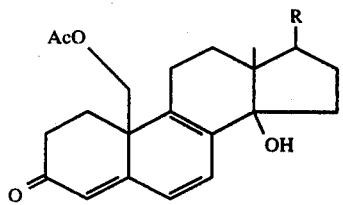

wherein R is as defined above;

(c) reducing a compound of the formula

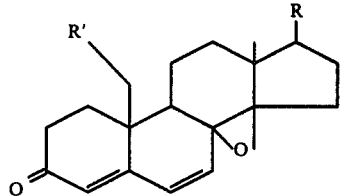

wherein R and R' are as defined above to form a compound of the formula

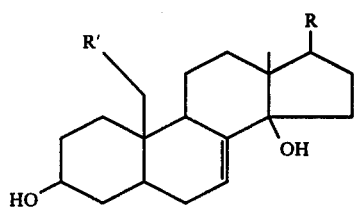

wherein R and R' are as defined above;

(d) reducing a compound of the formula

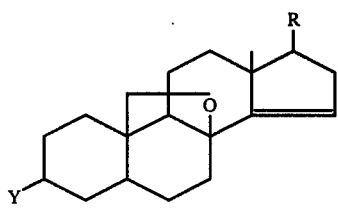

wherein R and Y are as defined above, to form a compound of the formula I,

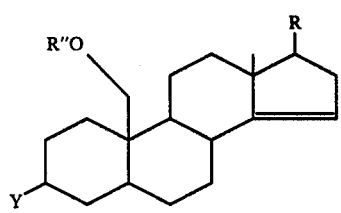

wherein R and Y are as defined above and R'' is H or Ac;

(e) subjecting a compound of the formula

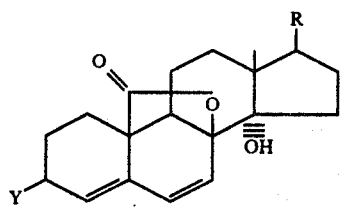

wherein R and Y are as defined above, to hydrogenolysis, to form a compound of the formula

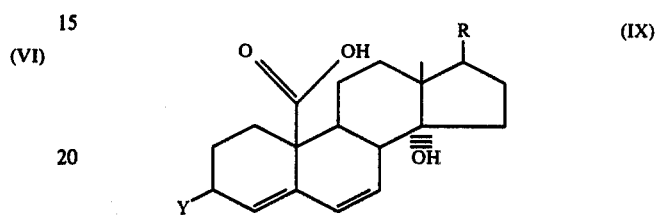

wherein R and Y are as defined above, hydrogenating the latter compound to form a compound of the formula

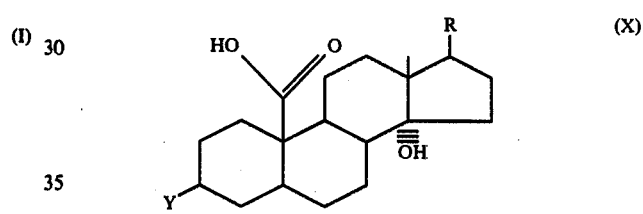

treating the latter with an acid or acid halide to form a compound of the formula

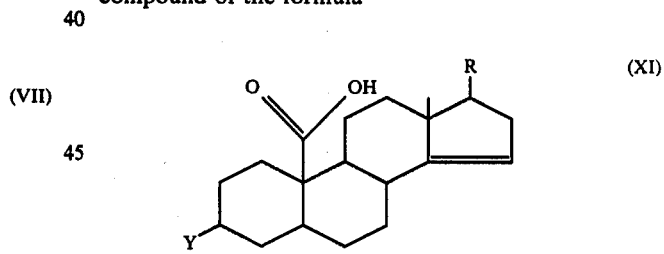

wherein R and Y are as defined above, and treating the latter with a reducing agent to form a compound of the formula I,

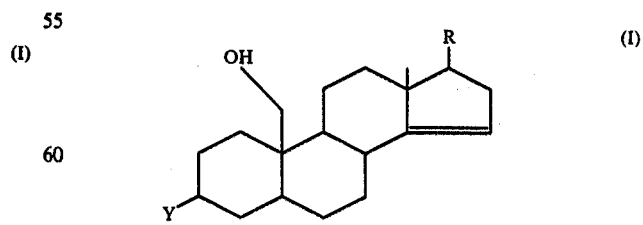

wherein R and Y are as defined above.

18. A process as defined in claim 17, wherein said process comprises reducing a compound of the formula

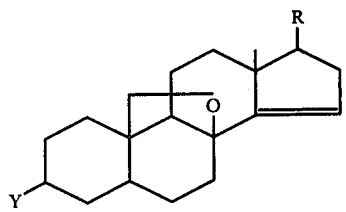
wherein R and Y are as defined above, to form a compound of the formula II
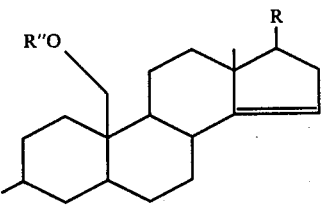
wherein R and Y are as defined above the R" is H, formyl or acetyl.
* * * * *